US010603370B2

(12) United States Patent
Ko et al.

(10) Patent No.: US 10,603,370 B2
(45) Date of Patent: Mar. 31, 2020

(54) COMPOSITIONS AND METHODS OF PREPARING *LEPTOSPIRA*

(71) Applicant: YALE UNIVERSITY, New Haven, CT (US)

(72) Inventors: Albert Ko, New Haven, CT (US); Elsio Wunder, Southbridge, MA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/166,689

(22) Filed: Oct. 22, 2018

(65) Prior Publication Data

US 2019/0105382 A1 Apr. 11, 2019

Related U.S. Application Data

(62) Division of application No. 15/124,633, filed as application No. PCT/US2015/019865 on Mar. 11, 2015, now Pat. No. 10,143,735.

(60) Provisional application No. 61/951,734, filed on Mar. 12, 2014.

(51) Int. Cl.

*A61K 39/39* (2006.01)
*A61K 39/02* (2006.01)
*A61K 39/295* (2006.01)
*A61K 39/00* (2006.01)

(52) U.S. Cl.

CPC ........ *A61K 39/0225* (2013.01); *A61K 39/295* (2013.01); *A61K 39/39* (2013.01); *A61K 2039/522* (2013.01); *A61K 2039/575* (2013.01); *A61K 2039/58* (2013.01); *Y02A 50/48* (2018.01)

(58) Field of Classification Search

None

See application file for complete search history.

(56) References Cited

U.S. PATENT DOCUMENTS 6,482,924 B1 11/2002 Utt et al.
2004/0043391 A1 3/2004 Utt et al.
2014/0023678 A1 1/2014 Pardo et al.

FOREIGN PATENT DOCUMENTS

WO 2013188936 A1 12/2013

OTHER PUBLICATIONS

International Search Report and Written Opinion for PCT International Application No. PCT/US2015/019865 dated Jul. 22, 2015.

UniProtKB entry Q72MM7 [retrieved on Jun. 30, 2015 from http://www.uniprot.org/uniprot/Q72MM7] ,2004.

Bromley, et al.,"Axial filament involvement in the motility of Leptospira interrogans," J Bacterial. 137 (3) , 1979 ,1406-1412.

Kunjantarachot, et al.,"Immunogenicity of Leptospira interrogans outer Membrane Vesicles in a Hamster Model," J. Vaccines Vaccin 5(4) ,2014 ,1-9.

Lambert, et al.,"FlaA Proteins in Leptospira Interrogans are Essential for Motility and Virulence but are not required for Formation of the Flagellum Sheath," Infection and Immunity ,2012 ,2019-2025.

Malmstrom,Johan et al.,"Proteome-wide cellular protein concentrations of the human pathogen Leptospira interrogans," Nature 460(7256) ,2009 ,762-765.

Picardeau,Mathieu et al.,First evidence for gene replacement in *Leptospira* spp. Inactivation of L. biflexa flaB results in non-motile mutants deficient in endoflagella,: Molecular Microbiology 40(1) ,2001 ,189-199.

Pinne, et al.,"The OmpL37 Surface-Exposed Protein Is Expressed by Pathogenic Leptospira during Infection and blinds Skin and Vascular Elastin," PLoS Negl Trop Dis. 4(9) ,2010 ,e815.

*Primary Examiner* — Jennifer E Graser

(74) *Attorney, Agent, or Firm* — Saul Ewing Arnstein & Lehr LLP; Kathryn Doyle; Justin Crotty

(57) ABSTRACT

The present invention includes compositions and methods of preparing flagellar-coiling protein 1 (Fcp1)-deficient *Leptospira* bacterium. In one aspect, the invention includes an isolated, flagellar-coiling protein 1 (Fcp1)-deficient *Leptospira* bacterium. Another aspect includes a composition comprising a flagellar-coiling protein 1 (Fcp1) deficient *Leptospira* bacterium. Yet another aspect includes a method of producing a motility-deficient *Leptospira* bacterium comprising inhibiting expression of a wild-type flagellar-coiling protein 1 (Fcp1) gene. Methods of stimulating an immune response and reducing or treating an infectious disease caused by one or more *Leptospira* bacteria in a subject in need thereof comprising administering a composition comprising an effective amount of flagellar-coiling protein 1 (Fcp1) deficient *Leptospira* bacteria to the subject are also included.

13 Claims, 10 Drawing Sheets

Specification includes a Sequence Listing.

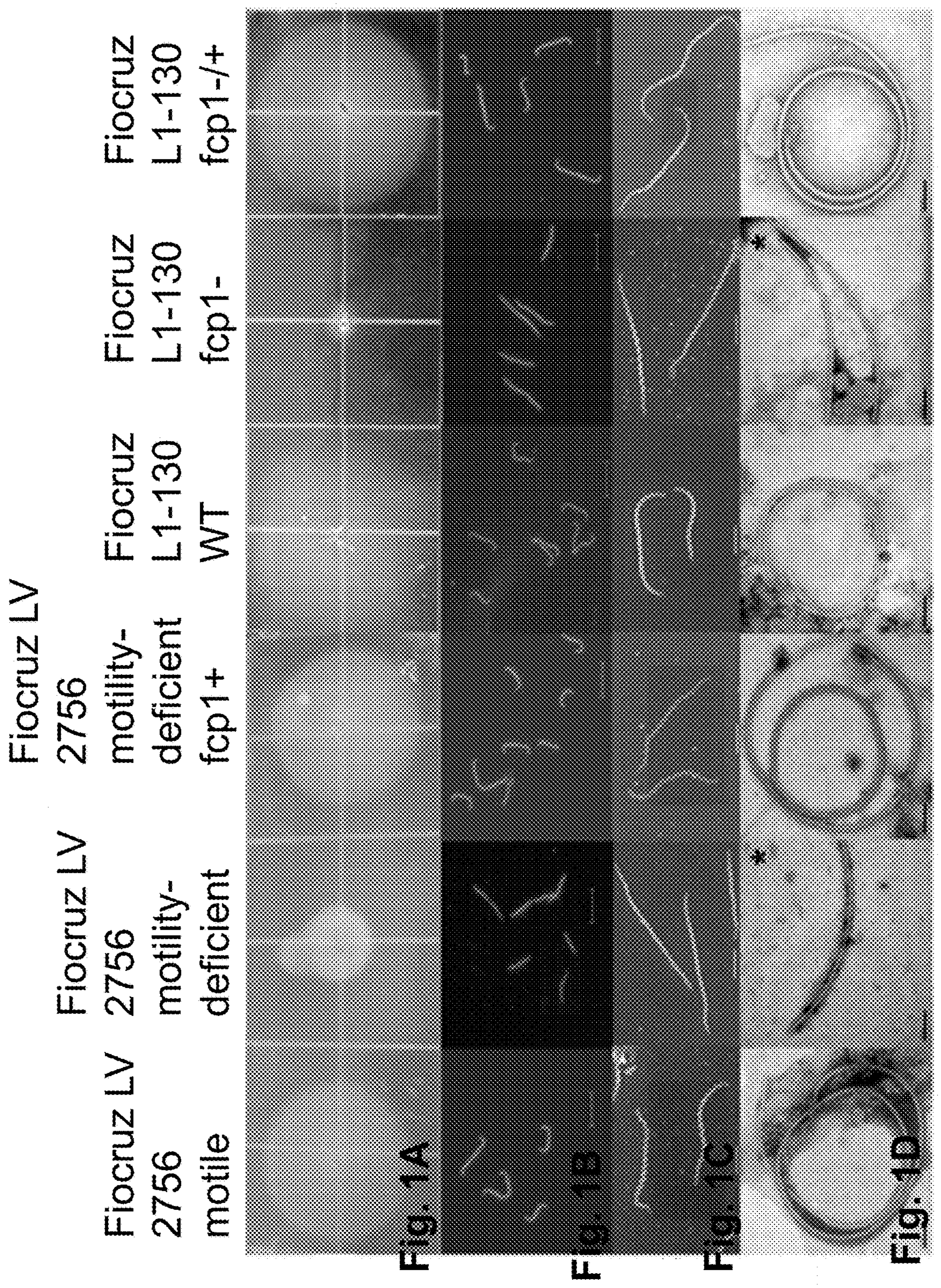
* Portion of the straight flagella

Fiocruz L1-130 wt

Fiocruz L1-130 fcp1⁻

Fiocruz L1-130 fcp1⁻/⁺
1μm

200nm

Fiocruz L1-130 fcp1⁻
OM
IM
Flagella (thin)

Fiocruz L1-130 fcp1⁻/⁺
OM
IM
Flagella (thick)

SEQUENCE LISTING

```
<160> NUMBER OF SEQ ID NOS: 16

<210> SEQ ID NO 1
<211> LENGTH: 921
<212> TYPE: DNA
<213> ORGANISM: Leptospira interrogans

<400> SEQUENCE: 1

gtgagcatta tgaaggtgat gaaaagcata ttcattcttc tggccgtgct gggactcaac      60

ctgtctgttt tagctcagca aaacaatcag ggcggtaatc agcaagccaa cgaatccgta     120

gaaaaaattg atgagctgtt aaaaggcgag ttggttcccg aagacgatga caaaaacctc     180
```

-continued

```
acggaagagc agaagcgtcg taaaaaagca attcaggaac aagaagctct gtggaaaaac    240

cctgatttta agggctatga taaaaatttc caagaactcc accaactctc caaagcattc    300

gcgaacaaca aatttaggtt ggcattatcc aattaccaat cgggcgttaa cacgattctt    360

aaaatgagag aagccataga acaataccgc aaagaagaag ctgaaaaaaa gcgtctcgat    420

gaaaagtggt actggcaaaa agtagatcgt aaggcgagag aagaccgtgt cgtttctaga    480

gacaaactag ttgccaaaca acaggcttta aattatttca ccaaggcgat caatcatttg    540

gatgaaatca aaaacccaga cttgagagaa agaccggagt tcaaaagact tctttccgat    600

acttacagat cttggatcct taccgaatac gatttacaaa atcttcctca gtgtatcccc    660

attctcgagc tctatatcga gatcgatgaa aatgaaaagg aatatcctgc tcataagtat    720

ctagcaagtt gttacgcttt cgaagaaaac atgatcaaaa agaatggtgg agcatccgaa    780

gatcagatgt tcaaataccg ttataagaaa aacgttcacc ttttgagagc gactgaactg    840

aagtatggaa aggattctcc cgaatacaaa cacatcgtta atcttgtaaa caaggacgaa    900

gtgatttcgg ttagacctta a                                              921


<210> SEQ ID NO 2
<211> LENGTH: 306
<212> TYPE: PRT
<213> ORGANISM: Leptospira interrogans

<400> SEQUENCE: 2

Met Ser Ile Met Lys Val Met Lys Ser Ile Phe Ile Leu Leu Ala Val
1               5                   10                  15

Leu Gly Leu Asn Leu Ser Val Leu Ala Gln Gln Asn Asn Gln Gly Gly
            20                  25                  30

Asn Gln Gln Ala Asn Glu Ser Val Glu Lys Ile Asp Glu Leu Leu Lys
        35                  40                  45

Gly Glu Leu Val Pro Glu Asp Asp Asp Lys Asn Leu Thr Glu Glu Gln
    50                  55                  60

Lys Arg Arg Lys Lys Ala Ile Gln Glu Gln Glu Ala Leu Trp Lys Asn
65                  70                  75                  80

Pro Asp Phe Lys Gly Tyr Asp Lys Asn Phe Gln Glu Leu His Gln Leu
                85                  90                  95

Ser Lys Ala Phe Ala Asn Asn Lys Phe Arg Leu Ala Leu Ser Asn Tyr
            100                 105                 110

Gln Ser Gly Val Asn Thr Ile Leu Lys Met Arg Glu Ala Ile Glu Gln
        115                 120                 125

Tyr Arg Lys Glu Glu Ala Glu Lys Lys Arg Leu Asp Glu Lys Trp Tyr
    130                 135                 140

Trp Gln Lys Val Asp Arg Lys Ala Arg Glu Asp Arg Val Val Ser Arg
145                 150                 155                 160

Asp Lys Leu Val Ala Lys Gln Gln Ala Leu Asn Tyr Phe Thr Lys Ala
                165                 170                 175

Ile Asn His Leu Asp Glu Ile Lys Asn Pro Asp Leu Arg Glu Arg Pro
            180                 185                 190

Glu Phe Lys Arg Leu Leu Ser Asp Thr Tyr Arg Ser Trp Ile Leu Thr
        195                 200                 205

Glu Tyr Asp Leu Gln Asn Leu Pro Gln Cys Ile Pro Ile Leu Glu Leu
    210                 215                 220

Tyr Ile Glu Ile Asp Glu Asn Glu Lys Glu Tyr Pro Ala His Lys Tyr
225                 230                 235                 240
```

```
Leu Ala Ser Cys Tyr Ala Phe Glu Glu Asn Met Ile Lys Lys Asn Gly
                245                 250                 255

Gly Ala Ser Glu Asp Gln Met Phe Lys Tyr Arg Tyr Lys Lys Asn Val
            260                 265                 270

His Leu Leu Arg Ala Thr Glu Leu Lys Tyr Gly Lys Asp Ser Pro Glu
        275                 280                 285

Tyr Lys His Ile Val Asn Leu Val Asn Lys Asp Glu Val Ile Ser Val
    290                 295                 300

Arg Pro
305


<210> SEQ ID NO 3
<211> LENGTH: 30
<212> TYPE: DNA
<213> ORGANISM: Artificial Sequence
<220> FEATURE:
<223> OTHER INFORMATION: Synthesized

<400> SEQUENCE: 3

cgggatcccg gatttcttgg gtcatttctt                                    30


<210> SEQ ID NO 4
<211> LENGTH: 30
<212> TYPE: DNA
<213> ORGANISM: Artificial Sequence
<220> FEATURE:
<223> OTHER INFORMATION: Synthesized

<400> SEQUENCE: 4

gctctagagc ttctctttca atggtattag                                    30


<210> SEQ ID NO 5
<211> LENGTH: 32
<212> TYPE: DNA
<213> ORGANISM: Artificial Sequence
<220> FEATURE:
<223> OTHER INFORMATION: Synthesized

<400> SEQUENCE: 5

cccaagcttg ggcgttcacc ttttgagagc ga                                 32


<210> SEQ ID NO 6
<211> LENGTH: 30
<212> TYPE: DNA
<213> ORGANISM: Artificial Sequence
<220> FEATURE:
<223> OTHER INFORMATION: Synthesized

<400> SEQUENCE: 6

ggactagtcc gcttcaatcg accgtttcca                                    30


<210> SEQ ID NO 7
<211> LENGTH: 22
<212> TYPE: DNA
<213> ORGANISM: Artificial Sequence
<220> FEATURE:
<223> OTHER INFORMATION: Synthesized

<400> SEQUENCE: 7

gctctagaaa cgcgtcccga gc                                            22


<210> SEQ ID NO 8
<211> LENGTH: 28
```

<212> TYPE: DNA
<213> ORGANISM: Artificial Sequence
<220> FEATURE:
<223> OTHER INFORMATION: Synthesized

<400> SEQUENCE: 8
cccaagctta acgcgtaaag taagcacc 28

<210> SEQ ID NO 9
<211> LENGTH: 28
<212> TYPE: DNA
<213> ORGANISM: Artificial Sequence
<220> FEATURE:
<223> OTHER INFORMATION: Synthesized

<400> SEQUENCE: 9
ggcgcgcctg gatcattgaa tagtctat 28

<210> SEQ ID NO 10
<211> LENGTH: 28
<212> TYPE: DNA
<213> ORGANISM: Artificial Sequence
<220> FEATURE:
<223> OTHER INFORMATION: Synthesized

<400> SEQUENCE: 10
ggcgcgccaa ggatcttggt tcgtaaaa 28

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11
aagcattacc gcttgtggtg 20

<210> SEQ ID NO 12
<211> LENGTH: 20
<212> TYPE: DNA
<213> ORGANISM: Artificial Sequence
<220> FEATURE:
<223> OTHER INFORMATION: Synthesized

<400> SEQUENCE: 12
gaactcccat ttcagcgatt 20

<210> SEQ ID NO 13
<211> LENGTH: 19
<212> TYPE: DNA
<213> ORGANISM: Artificial Sequence
<220> FEATURE:
<223> OTHER INFORMATION: Synthesized

<400> SEQUENCE: 13
aaagccagga caagcgccg 19

<210> SEQ ID NO 14
<211> LENGTH: 22
<212> TYPE: DNA
<213> ORGANISM: Artificial Sequence
<220> FEATURE:
<223> OTHER INFORMATION: Synthesized

<400> SEQUENCE: 14

-continued

```
ggttcacacc catcacaaac at                                             22


<210> SEQ ID NO 15
<211> LENGTH: 20
<212> TYPE: DNA
<213> ORGANISM: Artificial Sequence
<220> FEATURE:
<223> OTHER INFORMATION: Synthesized

<400> SEQUENCE: 15

ggtggagcca agagggtcat                                                20


<210> SEQ ID NO 16
<211> LENGTH: 24
<212> TYPE: DNA
<213> ORGANISM: Artificial Sequence
<220> FEATURE:
<223> OTHER INFORMATION: Synthesized

<400> SEQUENCE: 16

atctccgcac cttctgctga tgcc                                           24
```

COMPOSITIONS AND METHODS OF PREPARING *LEPTOSPIRA*

CROSS-REFERENCE TO RELATED APPLICATIONS

The present application is a divisional of, and claims priority to, U.S. patent application Ser. No. 15/124,633, filed Sep. 8, 2016, now U.S. Pat. No. 10,143,735, which is a 35 U.S.C. § 371 national phase application from, and claims priority to, International Application No. PCT/US2015/019865, filed Mar. 11, 2015, and published under PCT Article 21(2) in English, which is entitled priority under 35 U.S.C. § 119(e) to U.S. Provisional Application No. 61/951,734, filed Mar. 12, 2014, all of which applications are incorporated herein by reference in their entireties.

STATEMENT OF RIGHTS TO INVENTIONS MADE UNDER FEDERALLY SPONSORED RESEARCH

This invention was made with government support under AI0188752 and AI052473 awarded by National Institutes of Health. The government has certain rights in the invention.

BACKGROUND OF THE INVENTION

Leptospirosis is a life-threatening disease, which can occur in a diverse range of epidemiological situations. The spirochetal agent is a unique, albeit genetically and antigenically diverse group of bacteria divided into eight pathogenic *Leptospira* species and >200 serovars. The disease is considered the most widespread zoonosis in the world due to the pathogen's ability to induce a carrier state in a wide range of wild and domestic animals. Leptospires are highly motile bacteria, which can penetrate abraded skin and mucous membranes, causing a systemic infection in a short period of time by crossing tissue barriers and by haematogenous dissemination.

Spirochetes are one of the only phyla of bacteria that can be recognized and identified based on their unique and distinct corkscrew or helical morphologies. Cells of *Leptospira* spp., which have single short periplasmic flagella (PFs) at each end without overlapping at the center of the cell, exhibit a number of different shapes when moving. During translational motility, the anterior end is a spiral-shape and the posterior end is a hook-shaped, with translating cells rotating their PFs in opposite directions. Viewed from the center of the cell towards one of the cell ends, counterclockwise rotation results in the spiral-shaped end, and clockwise rotation results in the hook-shaped. They can readily reverse directions together with shape, and if the PFs are rotating in the same direction, the cells do not translate. When isolated in vitro and observed by negative-stain electron microscopy, PFs are extensively coiled in the form of a spring, and when the cells are at rest, fixed or dead, they differ from most other spirochetes for the presence of hook-shaped ends. Berg et al. (Berg et al., 1978, pp. 285-295, Cambridge: Cambridge University Press) proposed that in *Leptospira*, the PFs are more rigid when compared to the cell cylinder. Furthermore, previous studies showed that mutants that form uncoiled PFs, or without PFs, still maintain their helical shape, but have straight ends, which impairs their normal motility phenotype (Bromley et al., 1979, J Bacteriol 137, 1406-1412; Picardeau et al., 2001, Mol Microbiol 40, 189-199). Those results, taken together, indicate that the direction of rotation of PFs, and its interaction with the helically shaped cell cylinder determines a different conformation of the cell's ends, allowing them to move efficiently in both viscous media and low viscosity solvents.

PFs in spirochetes are known to be rather similar in structure and function to the flagella of other externally flagellated bacteria, as each consists of a basal body-motor complex, and a flexible hook region that connects to a helical flagellar filament. However, flagellar filaments of spirochete PFs are unique and complex, composed by multiple proteins, whereas in other swimming bacteria the Flagellin protein alone composes a thinner flagellar filament. A family of proteins named FlaB is consistently claimed to form the core of PF in spirochetes, and it shows sequence similarity with flagellin. However, spirochetes species have at least one additional set of proteins designated FlaA, which surrounds the inner core to form a sheath or partial sheath of *T. pallidum*, and *B. hyodysenteriae* PFs, but not in the sheath of *B. burgdorferi* PFs.

Although the function of the flagellar sheath is not clear, it has been suggested that it increases the stiffness of PFs, and that this produces a greater swimming velocity. In a more recent study, random mutants with disruption of both flaA genes in *L. interrogans* indicated that FlaA proteins have no involvement in the formation of the PFs sheath in this species.

Although motility and hook-deficient mutants were previously described, linking genes to protein function in these bacteria has been difficult due to the lack of tools for genetic manipulation of *Leptospira*.

Therefore, a need exists in the art for understanding the composition and architecture of PFs, and the role that motility plays in leptospiral virulence.

SUMMARY OF THE INVENTION

As described herein, the present invention includes methods and compositions of preparing flagellar-coiling protein 1 (Fcp1)-deficient *Leptospira* bacterium and methods of stimulating an immune response and reducing or treating an infectious disease caused by one or more *Leptospira* bacteria in a subject in need thereof.

One aspect of the invention includes an isolated, flagellar-coiling protein 1 (Fcp1)-deficient *Leptospira* bacterium. In another aspect, the invention includes a composition comprising a flagellar-coiling protein 1 (Fcp1) deficient *Leptospira* bacterium. In yet another aspect, the invention includes a vaccine comprising an effective amount of a motility deficient *Leptospira* bacteria. In still another aspect, the invention includes a composition for stimulating an immune response in a subject in need thereof comprising an effective amount of a motility deficient *Leptospira* bacteria.

In one aspect, the invention includes a method of stimulating an immune response in a subject in need thereof comprising administering a composition comprising an effective amount of a motility deficient *Leptospira* bacteria to the subject. In another aspect, the invention includes a method for reducing or treating an infectious disease caused by one or more *Leptospira* bacteria in a subject in need thereof comprising administering a composition comprising an effective amount of a motility deficient *Leptospira* bacteria to the subject.

In various embodiments of the above aspects or any other aspect of the invention delineated herein, the *Leptospira* bacterium comprises a silenced or deleted Fcp1 gene or a mutant Fcp1 gene. In one embodiment, the mutant Fcp1 gene expresses a mutant protein incapable of functioning as wildtype Fcp1. In another embodiment, the *Leptospira* bacterium is motility-deficient. In yet another embodiment, the *Leptospira* bacterium has attenuated bacterial virulence. In still another embodiment, the *Leptospira* bacterium is at least one of non-pathogenic, a live bacterium, and heat-inactivated.

In another embodiment, the *Leptospira* bacteria are at least one of live bacteria, heat-inactivated, and have attenuated bacterial virulence. In yet another embodiment, the *Leptospira* bacteria is deficit in a wild-type protein selected from the group consisting of flbB, flbD, flgA, flgB, flgC, flgD, flgG, flgH, flgI, flgM, flhA, flhB, flhF, flhX, fliA, fliE, fliF, fliG, fliG1, fliG3, fliH, fliI, fliJ, fliL, fliM, fliN, fliO, flip, fliQ, fliR, motA, motA1, motB, motB, flgE, flgJ, flgK, flgL, flhO, fliD, fliK, fcp1, fcp2, flaA1, flaA2, flaB1, flaB2, flaB3, flaB4, fliS, and any combination thereof.

In various embodiments of the above aspects or any other aspect of the invention delineated herein, the composition further comprises a pharmaceutically acceptable carrier. In one embodiment, the composition further comprises an adjuvant, such as an oil-in-water emulsion, a saponin, a cholesterol, a phospholipid, a CpG, a polysaccharide, variants thereof, and a combination thereof.

Another aspect of the invention includes a method of producing a motility-deficient *Leptospira* bacterium comprising inhibiting expression of a wild-type flagellar-coiling protein 1 (Fcp1) gene.

In various embodiments of the above aspects or any other aspect of the invention delineated herein, inhibiting expression of the wild-type Fcp1 gene comprises deleting or silencing the wild-type Fcp1 gene in the *Leptospira* bacterium. In another embodiment, inhibiting expression of the wild-type Fcp1 gene comprises mutating the wild-type Fcp1 gene in the *Leptospira* bacterium. In such an embodiment, the mutant Fcp1 gene expresses a mutant Fcp1 protein incapable of functioning as wildtype Fcp1 protein.

BRIEF DESCRIPTION OF THE DRAWINGS

FIG. 1A is a panel of pictures showing motility assays using 0.5% agarose EMJH medium. Approximately $10^5$ leptospires were inoculated, and plates were incubated for 10 days at 30° C. Each square has 1 cm;

FIG. 1B is a panel of pictures showing the morphology of the clones observed by dark field microscopy using 100× oil objective and dark field oil condenser;

FIG. 1C is a panel of scans showing the morphology of the cells observed by scanning electron microscopy;

FIG. 1D is a panel of scans showing the morphology of purified periplasmic flagella (PF) observed by transmission electron microscopy using 2% phosphotungstic acid (PTA) negative staining.

DETAILED DESCRIPTION OF THE INVENTION

Definitions

Figure 2A:
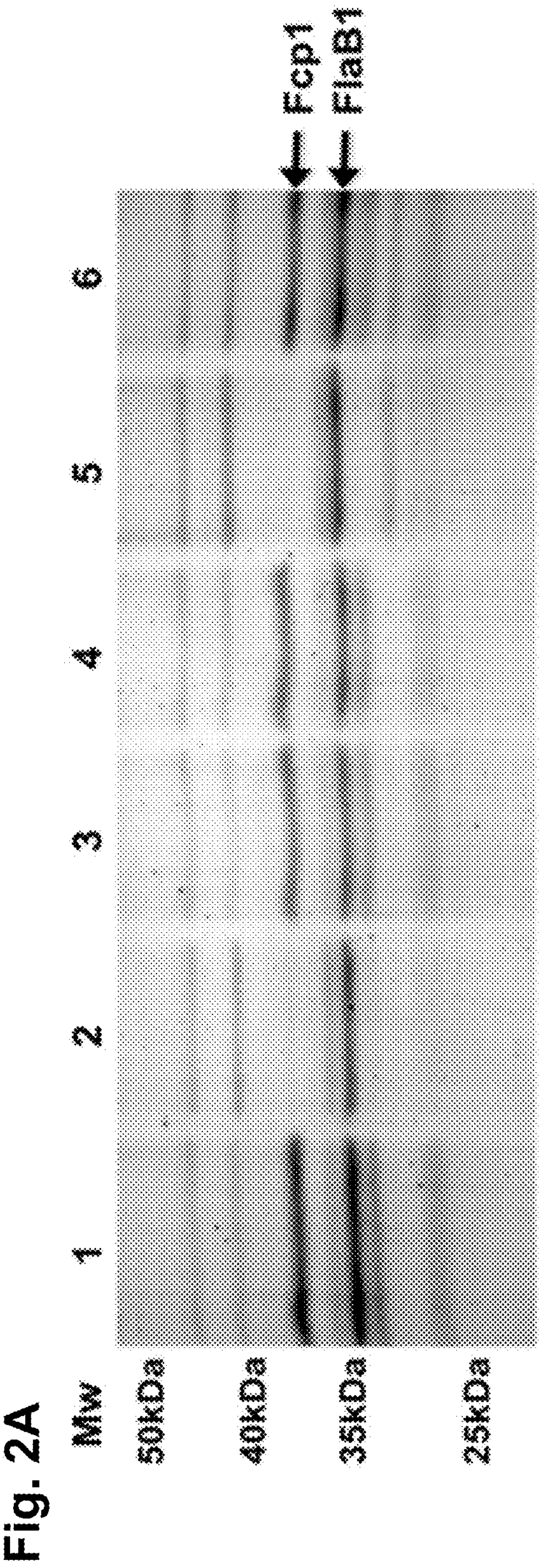
FIG. 2A is a gel showing the detection of Fcp1 expression. *L. interrogans* Fiocruz LV 2756 motile (lane 1), *L. interrogans* Fiocruz LV 2756 motility-deficient (lane 2), *L. interrogans* Fiocruz LV 2756 motility-deficient fcp1$^+$ (lane 3), *L. interrogans* Fiocruz L1 130 WT (lane 4), *L. interrogans* Fiocruz L1 130 fcp1$^-$ (lane 5), and *L. interrogans* Fiocruz L1 130 fcp1$^{-/+}$ (lane 6). SDS/PAGE. Arrows indicate the position of the proteins identified by mass spectrometry.

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

The term "antibody," as used herein, refers to an immunoglobulin molecule which specifically binds with an antigen. Antibodies include intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By "attenuated" is meant the bacterium has a decreased virulence with respect to a wild-type bacterium. In particular, a bacterium has an attenuated virulence of about 10, 20, 30, 40, 50, 60, 70, 80% or more decrease in virulence as compared to a wild-type bacterium.

By "flagellar-coiling protein 1 gene" or "Fcp1 gene" is meant a nucleic acid molecule encoding a Fcp1 gene or fragment thereof. An exemplary Fcp1 gene sequence corresponds to a hypothetical protein coded by the gene LIC13166 found on chromosome 1 of a *L. interrogans* serovar Copenhageni strain 2756 in the GenBank Accession No. NC_005823 and is provided in SEQ ID NO:1 and below:

```
1   gtgagcatta tgaaggtgat gaaaagcata ttcattcttc tggccgtgct gggactcaac
61  ctgtctgttt tagctcagca aaacaatcag ggcggtaatc agcaagccaa cgaatccgta
121 gaaaaaattg atgagctgtt aaaaggcgag ttggttcccg aagacgatga caaaaacctc
181 acggaagagc agaagcgtcg taaaaaagca attcaggaac aagaagctct gtggaaaaac
241 cctgatttta agggctatga taaaaatttc caagaactcc accaactctc caaagcattc
301 gcgaacaaca aatttaggtt ggcattatcc aattaccaat cgggcgttaa cacgattctt
361 aaaatgagag aagccataga acaataccgc aaagaagaag ctgaaaaaaa gcgtctcgat
421 gaaaagtggt actggcaaaa agtagatcgt aaggcgagag aagaccgtgt cgtttctaga
481 gacaaactag ttgccaaaca acaggcttta aattatttca ccaaggcgat caatcatttg
541 gatgaaatca aaaacccaga cttgagagaa agaccggagt tcaaaagact tctttccgat
601 acttacagat cttggatcct taccgaatac gatttacaaa atcttcctca gtgtatcccc
661 attctcgagc tctatatcga gatcgatgaa aatgaaaagg aatatcctgc tcataagtat
```

-continued

```
721   ctagcaagtt gttacgcttt cgaagaaaac atgatcaaaa agaatggtgg agcatccgaa
781   gatcagatgt tcaaataccg ttataagaaa aacgttcacc ttttgagagc gactgaactg
841   aagtatggaa aggattctcc cgaatacaaa cacatcgtta atcttgtaaa caaggacgaa
901   gtgatttcgg ttagacctta a
```

As used herein, the term "fragment" as applied to a nucleic acid, is less than about 950 nucleotides in length or less than the whole Fcp1 gene. In one embodiment, a fragment is between about 700 nucleotides to about 900 nucleotides in length, preferably, between at least about 600 nucleotides to about 950 nucleotides in length, more preferably, between about at least about 500 nucleotides to about 1000 nucleotides in length, even more preferably, between at least about 200 nucleotides to about 700 nucleotides, yet even more preferably, between at least about 100 nucleotides to about 950 nucleotides, and yet even more preferably, between at least about 50 nucleotides to about 1000 nucleotides in length, and most preferably, the nucleic acid fragment will be greater than about 700 nucleotides in length.

By "flagellar-coiling protein 1 protein" or "Fcp1 protein" is meant a protein or fragment thereof having at least about 85% amino acid identity to the hypothetical protein LIC13166 encoded by the gene LIC13166 found on chromosome 1 of a *L. interrogans* serovar Copenhageni strain 2756 in the amino acid sequence of GenBank Accession No. YP_003074.1, or a fragment thereof, and having at least one Fcp1 protein biological activity. In one embodiment, a Fcp1 protein has at least about 85% amino acid sequence identity to SEQ ID NO:2 and the following amino acid sequence:

as membrane proteins, ribosomes, and nucleic acids, occurs. Heat-inactivated bacteria have attenuated virulence and may be non-pathogenic.

As applied to the nucleic acid or protein, "homologous" as used herein refers to a sequence that has about 50% sequence identity. More preferably, the homologous sequence has about 75% sequence identity, even more preferably, has at least about 80%, 85%, 90%, 91%, 92%, 93%, 94%, 95%, 96%, 97%, 98%, 99% sequence identity.

By "host" or "host cell" is meant a cell, such as a mammalian cell, that harbors a pathogen, such as a *Leptospira* bacterium. The pathogen can infect the host cell is capable of infecting.

By "immune response" is meant the actions taken by a host to defend itself from pathogens or abnormalities. The immune response includes innate (natural) immune responses and adaptive (acquired) immune responses. Innate responses are antigen non-specific. Adaptive immune responses are antigen specific. An immune response in an organism provides protection to the organism against *Leptospira* bacterial infections when compared with an otherwise identical subject to which the composition or cells were not administered or to the human prior to such administration.

```
  1   msimkvmksi fillavlgln lsvlaqqnnq ggnqqanesv ekidellkge lvpedddknl
 61   teeqkrrkka iqeqealwkn pdfkgydknf qelhqlskaf annkfrlals nyqsgvntil
121   kmreaieqyr keeaekkrld ekwywqkvdr karedrvvsr dklvakqqal nyftkainhl
181   deiknpdlre rpefkrllsd tyrswiltey dlqnlpqcip ilelyieide nekeypahky
241   lascyafeen mikknggase dqmfkyrykk nvhllratel kygkdspeyk hivnlvnkde
301   visvrp
```

As applied to a protein, a "fragment" of Fcp1 protein is about 50 amino acids in length. More preferably, the fragment of Fcp1 protein is about 75 amino acids, even more preferably, at least about 100, yet more preferably, at least about 125, even more preferably, at least about 150, yet more preferably, at least about 200, even more preferably, about 225, and more preferably, at least about 250, and more preferably, at least about 300 amino acids in length amino acids in length.

By "Fcp1 deficient" is meant a bacterium that lacks wildtype Fcp1 proteins or lacks the wildtype Fcp1 gene. For example, a *Leptospira* bacterium that has a Fcp1 gene that is silenced is Fcp1 deficient in wildtype Fcp1 protein. In another embodiment, a *Leptospira* bacterium that has a deleted Fcp1 gene is Fcp1 deficient in both the Fcp1 gene and Fcp1 proteins. In another embodiment, a *Leptospira* bacterium that has a mutated Fcp1 gene is Fcp1 deficient in both the wildtype Fcp1 gene and wildtype Fcp1 proteins.

By "heat-inactivated" refers to the process or method of heating a pathogen, such as bacteria, to temperatures sufficiently high that irreversible denaturation of proteins, such By "infection" is meant a bacterial colonization of the host. Infection of a host can occur by entry of the bacterium or bacteria through a break in barrier epithelial surfaces, such as unhealed breaks in the skin, the eyes, or with the mucous membranes.

By "*Leptospira* bacterium" or "*Leptospira* bacteria" is meant a spirochete bacterium or bacteria. *Leptospira* bacteria are very thin, tightly coiled, obligate aerobic spirochetes characterized by a unique flexuous type of motility. *Leptospira* bacterium is a gram-negative spirochete with internal flagella. The genus is divided into two species: the pathogenic leptospires *L. interrogans* and the free-living leptospire *L. biflexa*. Serotypes of *L. interrogans* are the agents of leptospirosis, a zoonotic disease.

By "functional" or "functioning" is meant to have at least one Fcp1 protein biological activity.

By "motility-deficient" is meant the inability of a *Leptospira* bacterium to move or swim in a solution having a certain viscosity. Examples of genes that affect motility in *Leptospira* bacterium include, but are not limited to, flbB, flbD, flgA, flgB, flgC, flgD, flgG, flgH, flgI, flgM, flhA, flhB, flhF, flhX, fliA, fliE, fliF, fliG, fliG1, fliG3, fliH, fliI, fliJ, fliL, fliM, fliN, fliO, flip, fliQ, fliR, motA, motA1, motB, motB, flgE, flgJ, flgK, flgL, flhO, fliD, fliK, fcp1, fcp2, flaA1, flaA2, flaB1, flaB2, flaB3, flaB4, fliS, and any combination thereof.

By "mutant" or "mutated" is meant a change of the nucleotide sequence in a gene of a *Leptospira* bacterium, such as a flagellar-coiling protein 1 (Fcp1) gene. The mutant or mutated gene can result in several different types of change in sequences, such as altering the Fcp1 protein, or preventing a gene from functioning properly or completely. Mutations can also occur in nongenic regions of a gene, such that expression of a gene is altered, decreased, or not expressed.

By "pathogen" is meant an infectious agent, such as *Leptospira* bacteria, capable of causing infection, producing toxins, and/or causing disease in a host.

By "silence" or "silenced" is meant that expression of the Fcp1 gene is prevented or decreased. Fcp1 gene silencing can occur via a gene knockdown, such as RNAi. When genes are knocked down, their expression is decreased by at least 10, 20, 30, 40, 50, 60, 70, 80, 90% or more.

By the term "vaccine" as used herein, is meant a composition, a bacterium, a protein, or a nucleic acid of the invention, which serves to protect an animal against a *Leptospira* bacterial disease and/or to treat an animal already infected with *Leptospira* bacteria compared with an otherwise identical animal to which the vaccine is not administered or compared with the animal prior to the administration of the vaccine.

By "virulence" is meant a degree of pathogenicity of a given pathogen or the ability of an organism to cause disease in another organism. Virulence refers to an ability to invade a host organism, cause disease, evade an immune response, and produce toxins.

By "bacterial virulence" is meant a degree of pathogenicity of bacteria, such as *Leptospira* bacteria. Bacterial virulence includes causing infection or disease in a host, producing agents that cause or enhance disease in a host, producing agents that cause or enhance disease spread to another host, and causing infection or disease in another host.

By "virulent" or "pathogenic" is meant a capability of a bacterium to cause a severe disease.

By "non-pathogenic" is meant an inability to cause disease.

By "wildtype" is meant a non-mutated version of a gene, allele, genotype, polypeptide, or phenotype, or a fragment of any of these. It may occur in nature or produced recombinantly.

By "wildtype Fcp1" is meant a nucleic acid molecule, a gene or a protein that contains a native Fcp1 nucleic acid sequence, gene, or amino acid sequence.

By "infectious disease" is meant a disease or condition in a subject caused by a pathogen that is capable of being transmitted or communicated to a non-infected subject. Non-limiting examples of infectious diseases include bacterial infections, viral infections, fungal infections, and the like.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "portion" of a polynucleotide means at least at least about twenty sequential nucleotide residues of the polynucleotide. It is understood that a portion of a polynucleotide may include every nucleotide residue of the polynucleotide.

By "effective amount" is meant the amount required to reduce or improve at least one symptom of a disorder, condition or disease relative to an untreated patient. The effective amount used for therapeutic treatment of a condition or disease or stimulating an immune response, varies depending upon the manner of the specific disorder, condition or disease, extent of the disorder, condition or disease, and administration of the cells, as well as the age, body weight, and general health of the subject.

The term "expression" as used herein is defined as the transcription and/or translation of a particular nucleotide sequence driven by its promoter.

The term "isolated" refers to a material or an organism, such as bacteria, that is free to varying degrees from components or other organisms which normally accompany it as found in its native state. Isolated denotes a degree of separation from an original source or surroundings. An isolated bacterium is sufficiently free of other bacteria such that any contaminants do not materially affect growth, pathogencity, infection, etc. or cause other adverse consequences. That is, bacteria are isolated if they are substantially free of bacteria or materials. Purity and homogeneity are typically determined using analytical techniques, for example, single cell culturing. The term "purified" can denote that a cell gives rise to essentially one population.

"Proliferation" is used herein to refer to the reproduction or multiplication of similar forms, especially of bacteria. That is, proliferation encompasses production of a greater number of bacteria, and can be measured by, among other things, simply counting the numbers of bacteria, measuring incorporation of $^3$H-thymidine into the bacteria, and the like.

As used herein, "sample" or "biological sample" refers to anything, which may contain the cells of interest (e.g., cancer or tumor cells thereof) for which the screening method or treatment is desired. The sample may be a biological sample, such as a biological fluid or a biological tissue. In one embodiment, a biological sample is a tissue sample including pulmonary arterial endothelial cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

A "subject" as used therein, may be a human or non-human mammal. Non-human mammals include, for example, livestock and pets, such as ovine, bovine, porcine, canine, feline and murine mammals. Preferably, the subject is human.

As used herein, the terms "treat," treating," "treatment," and the like refer to reducing or improving an infectious disease or condition and/or one or more symptoms associated therewith. It will be appreciated that, although not precluded, treating an infectious disease or condition and/or one or more symptoms associated therewith does not require that the disorder, condition, disease or symptoms associated therewith be completely ameliorated or eliminated.

A "vector" is a composition of matter that comprises the Fcp1 gene and that may be used to deliver the Fcp1 gene to the interior of a cell. Vector refers to any plasmid containing the Fcp1 gene that is capable of moving foreign sequences into the genomes of a target organism or cell.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

*Leptospira*

It has been discovered that flagellar-coiling protein 1 (Fcp1) plays an integral role in *Leptospira* flagella. Functional loss of Fcp1 in *Leptospira* bacteria leads to motility deficiency and impaired bacterial virulence. The invention includes, in one aspect, an isolated, flagellar-coiling protein 1 (Fcp1)-deficient *Leptospira* bacterium.

In one embodiment, the *Leptospira* bacterium comprises a silenced or deleted Fcp1 gene. When silencing is employed, the expression of the Fcp1 gene is prevented or decreased. An exemplary example of gene silencing is through a gene knockdown, such as RNAi. In another embodiment, the *Leptospira* bacterium comprises a mutant Fcp1 gene. In instances when the Fcp1 gene is mutated, the mutant Fcp1 gene may express a mutant protein incapable of functioning as wildtype Fcp1.

Motility-deficient *Leptospira* bacteria are also included in the invention. The isolated, Fcp1 deficient *Leptospira* bacteria possessed thinner periplasmic flagella than wildtype counterparts. The thinner flagella lack tensile strength to generate sufficient thrust for motility of the bacterium. Motility is essential for penetration into a host mucosa to establish infection. The invention also includes a *Leptospira* bacterium that has attenuated bacterial virulence. In another embodiment, the invention includes a *Leptospira* bacterium that is non-pathogenic.

Another aspect of the invention includes a composition comprising a flagellar-coiling protein 1 (Fcp1)-deficient *Leptospira* bacterium. In one embodiment, the composition includes the *Leptospira* bacterium comprising a silenced or deleted Fcp1 gene. In another embodiment, the *Leptospira* bacterium comprises a mutant Fcp1 gene. In some embodiments when the *Leptospira* bacterium includes a mutant Fcp1 gene, the mutant Fcp1 gene expresses a mutant protein incapable of functioning as wildtype Fcp1 protein.

The invention also includes an embodiment where the composition comprises a *Leptospira* bacterium that is motility-deficient. In another embodiment, the *Leptospira* bacterium has attenuated bacterial virulence. In yet another embodiment, the *Leptospira* bacterium is non-pathogenic.

In another embodiment, the composition stimulates production of an antibody against the motility deficient *Leptospira* bacteria in the subject. The antibody produced confers protection against infection by a heterologous pathogen, such as a different *Leptospira* bacteria, in the subject or a new subject when transferred. The antibody produced can be of any class, such as IgG, IgM, or IgA or any subclass such as IgG1, IgG2a, and other subclasses known in the art. The antibodies may be transferred without purification, or isolated, purified, or otherwise obtained from the original subject using methods known in the art. The antibodies can then be administered to a second subject for protection against *Leptospira* bacteria or a heterologous pathogen.

The invention also includes vaccines and compositions that can be formulated for use as vaccines. In one embodiment, a vaccine comprises an effective amount of a motility deficient *Leptospira* bacteria. In another embodiment, a composition for stimulating an immune response in a subject in need thereof comprises an effective amount of a motility deficient *Leptospira* bacteria. The *Leptospira* bacteria of the composition is deficit in at lease one wild-type protein, such as, but not limited to, flbB, flbD, flgA, flgB, flgC, flgD, flgG, flgH, flgI, flgM, flhA, flhB, flhF, flhX, fliA, fliE, fliF, fliG, fliG1, fliG3, fliH, fliI, fliJ, fliL, fliM, fliN, fliO, flip, fliQ, fliR, motA, motA1, motB, motB, flgE, flgJ, flgK, flgL, flhO, fliD, fliK, fcp1, fcp2, flaA1, flaA2, flaB1, flaB2, flaB3, flaB4, fliS, and any combination thereof. The composition also includes a *Leptospira* bacterium that is a live bacterium. In another embodiment, the *Leptospira* bacterium is heat-inactivated. In yet another embodiment, the *Leptospira* bacterium has attenuated bacterial virulence.

The invention also includes a composition that further includes a pharmaceutically acceptable carrier. In another embodiment, the composition further includes an adjuvant, such as an oil-in-water emulsion, a saponin, a cholesterol, a phospholipid, a CpG, a polysaccharide, variants thereof, and a combination thereof.

Methods

The present invention also includes, in one aspect, a method of producing a motility-deficient *Leptospira* bacterium. As described herein, the method comprises inhibiting expression of a wild-type flagellar-coiling protein 1 (Fcp1) gene.

In one embodiment, inhibiting expression of the wild-type Fcp1 gene comprises deleting or silencing the wild-type Fcp1 gene in the *Leptospira* bacterium.

In another embodiment, inhibiting expression of the wild-type Fcp1 gene comprises mutating the wild-type Fcp1 gene in the *Leptospira* bacterium. In this and other embodiments, the mutant Fcp1 gene expresses a mutant Fcp1 protein incapable of functioning as wildtype Fcp1 protein.

In another aspect, the invention includes a method of stimulating an immune response in a subject in need thereof comprising administering a composition comprising an effective amount of a motility-deficient *Leptospira* bacteria to the subject. In yet another aspect, the invention includes a method for reducing or treating an infectious disease caused by one or more *Leptospira* bacteria in a subject in need thereof comprising administering a composition comprising an effective amount of a motility-deficient *Leptospira* bacteria to the subject. In one embodiment, the *Leptospira* bacteria is deficit in a wild-type protein that functions in motility, such as but not limited to, flbB, flbD, flgA, flgB, flgC, flgD, flgG, flgH, flgI, flgM, flhA, flhB, flhF, flhX, fliA, fliE, fliF, fliG, fliG1, fliG3, fliH, fliI, fliJ, fliL, fliM, fliN, fliO, flip, fliQ, fliR, motA, motA1, motB, motB, flgE, flgJ, flgK, flgL, flhO, fliD, fliK, fcp1, fcp2, flaA1, flaA2, flaB1, flaB2, flaB3, flaB4, fliS, and any combination thereof.

In one embodiment, administering the composition comprises producing antibodies against the motility deficient *Leptospira* bacteria. The production of antibodies may be short lived or long lasting within the subject. Short lived antibody responses may be maintained over time by administration of motility deficient *Leptospira* bacteria or boosts to the immune response, such as through repetitive administrations of the motility deficient *Leptospira* bacteria. The antibodies generated may confer protection against infection by a heterologous pathogen, such as a different *Leptospira* bacteria, in the subject or or a new subject when transferred. The antibodies generated can be of any class, such as IgG, IgM, or IgA or any, subclass such as IgG1, IgG2a, and other subclasses known in the art. In another embodiment, the method further comprises isolating the antibodies from the subject and transferring the antibodies to a new subject. The antibodies may be transferred without purification, or isolated, purified, or otherwise obtained from the original subject by methods known in the art. The antibodies may further be administered to the second subject for protection against *Leptospira* bacteria or a heterologous pathogen. The administration of the antibodies may be through any methods known in the art of administering antibodies.

Antigens that stimulate an immune response, yet do not produce pathogenic disease in a subject, are exemplary vaccine candidates. Included in the methods of the invention are *Leptospira* bacteria that can stimulate an immune response, such as motility-deficient *Leptospira* bacteria. In one embodiment, the administered *Leptospira* bacteria are live bacteria. In another embodiment, the *Leptospira* bacteria are heat-inactivated. In yet another embodiment, the *Leptospira* bacteria have attenuated bacterial virulence. In yet another embodiment, the *Leptospira* bacteria are non-pathogenic.

The methods also include administering an adjuvant, separately or in tandem with the compositions, such as an oil-in-water emulsion, a saponin, a cholesterol, a phospholipid, a CpG, a polysaccharide, variants thereof, and a combination thereof, with the composition of the invention.

Pharmaceutical formulations that are useful in the methods of the invention may be suitably developed for inhalational, oral, parenteral, pulmonary, intranasal, intravenous or another route of administration. Other contemplated formulations include projected nanoparticles, liposomal preparations, and immunologically-based formulations. The route(s) of administration will be readily apparent to the skilled artisan and will depend upon any number of factors including the type and severity of the disease being treated, the type and age of the veterinary or human patient being treated, and the like.

The pharmaceutical formulations described herein may be prepared by any method known or hereafter developed in the art of pharmacology. In general, such preparatory methods include the step of bringing the cells into association with a carrier or one or more other accessory ingredients, and then, if necessary or desirable, shaping or packaging the product into a desired single- or multi-dose unit.

In one embodiment, the cells of the invention are formulated using one or more pharmaceutically acceptable excipients or carriers. In one embodiment, the pharmaceutical formulations of the cells of the invention include a therapeutically effective amount of the cells of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

Administration/Dosing

In the clinical settings, delivery systems for the compositions described herein can be introduced into a subject by any of a number of methods, each of which is familiar in the art. For instance, a pharmaceutical formulation of the composition can be administered by inhalation or systemically, e.g. by intravenous injection.

The regimen of administration may affect what constitutes an effective amount. The therapeutic formulations may be administered to the subject either prior to or after the manifestation of symptoms associated with the disease or condition. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the composition of the present invention to a subject, preferably a mammal, more preferably a human, may be carried out using known procedures, at dosages and for periods of time effective to treat a disease or condition in the subject. An effective amount of the composition necessary to achieve a therapeutic effect may vary according to factors such as the extent of implantation; the time of administration; the duration of administration; other drugs, compounds or materials used in combination with the composition; the state of the disease or disorder; age, sex, weight, condition, general health and prior medical history of the subject being treated; and like factors well-known in the medical arts. Dosage regimens may be adjusted to provide the optimum therapeutic response. For example, several divided doses may be administered daily or the dose may be proportionally reduced as indicated by the exigencies of the therapeutic situation. One of ordinary skill in the art would be able to study the relevant factors and make the determination regarding the effective amount of the composition without undue experimentation.

Actual dosage levels of the cells in the pharmaceutical formulations of this invention may be varied so as to obtain an amount of the composition that are effective to achieve the desired therapeutic response for a particular subject, composition, and mode of administration, without being toxic to the subject.

Routes of Administration

Routes of administration of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable formulation of the composition sand dosages include, for example, dispersions, suspensions, solutions, beads, pellets, magmas, creams, pastes, plasters, lotions, discs, suppositories, liquid sprays for nasal or oral administration, aerosolized formulations for inhalation, compositions and formulations for intravesical administration and the like.

It should be understood that the formulations and compositions that would be useful in the present invention are not limited to the particular formulations set forth in the examples. The following examples are put forth so as to provide those of ordinary skill in the art with a complete disclosure and description of how to make and use the cells, differentiation methods, engineered tissues, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out embodiments of the present invention, and are not to be construed as limiting in any way.

The Materials and Methods used in the performance of the experiments disclosed herein are now described.

Bacterial Strains and Cloning Procedure.

The strains of *L. interrogans* used in this study, including the mutants, were grown to a mid log-phase in liquid Ellinghausen-McCullough-Johnson-Harris (EMJH) medium (Ellinghausen et al., 1965, Am J Vet Res 26, 45-51) at 29° C.

In order to obtain clones for further studies in genetics of leptospirosis, *L. interrogans* serovar Copenhageni strain LV 2756, a virulent clinical isolate recently cultivated from the blood of a patient with severe pulmonary hemorrhagic syndrome (SPHS) (Gouveia et al., 2008, Emerg Infect Dis 14, 505-508), and *L. interrogans* serovar Copenhageni strain Fiocruz L1-130 (Nascimento et al., 2004, Braz J Med Biol Res 37, 459-477), both enrolled in the hospital-based surveillance study in Salvador, Brazil (Ko et alk, 1999, Lancet 354, 820-825), were plated in 1% agar plates of Ellinghausen-McCullough-Johnson-Harris (EMJH) medium (Ellinghausen et al., 1965, Am J Vet Res 26, 45-51; Johnson et al., 1967, J Bacteriol 94, 27-31), in a concentration of 100 and 10 leptospires, after determination of the number of cells per mL using a Petroff-Hausser counting chamber (Fisher Scientific). Plates were incubated at 29° C., and visualized weekly during a period of 4 weeks. The colonies obtained were cultivated in liquid EMJH at 29° C., and observed under dark-field microscopy.

*E. coli* strains were grown in Luria-Bertani (LB) medium. When necessary, spectinomycin and/or kanamycin were added to culture media at a concentration of 50 μg/mL.

Genomic DNA was extracted from a pellet of 5 mL cultures using the Maxwell®16 (Promega Corporation, Madison, Wis.).

Construction of Mutant and Complemented Strain.

Mutagenesis experiments were performed using the conjugation method (Picardeau, 2008, Appl Environ Microbiol 74, 319-322), and for colonies selection, 1% agar plates of EMJH. Strains of *E. coli* used for the mutagenesis experiments were grown in Luria-Bertani (LB) medium. When necessary, spectinomycin and/or kanamycin were added at a concentration of 50 μg/mL in both culture media.

For allelic exchange of the fcp1 gene, an upstream and downstream region of the gene were amplified from the genomic DNA of *L. interrogans* serovar Copenhageni strain Fiocruz L1-130 using primers Fcp1_FlkAF and Fcp1_FlkAR for the upstream region, and Fcp1_FlkBF and Fcp1_FlkBR for the downstream region. See Table 1. The PCR products of upstream and downstream region were digested with BamHI and XbaI, and HindIII and SpeI, respectively. The Spcr cassette was amplified using primers Spc_Xba5 and Spc_Hind3, and the PCR product was digested with XbaI and HindIII. The three digested PCR products were transformed into the non-replicative plasmid pSW29T (Picardeau, 2008, Appl Environ Microbiol 74, 319-322), previously digested with BamHI and SpeI. The final plasmid, containing the flanking regions of the fcp1 gene, which was replaced by the Spcr cassette, was transfected into the donor strain *E. coli* (32163 cells, and introduced into strain Fiocruz L1-130 by conjugation, as previously described (Picardeau, 2008, Appl Environ Microbiol 74, 319-322). After 4 to 6 weeks of plate incubation at 30° C., spectinomycin-resistant transformants were inoculated into liquid EMJH supplemented with 50 μg/ml of spectinomycin, and examined for allelic exchange in the target gene by PCR, using primers Fcp1_AscF and Fcp1_AscR, and by Western blotting. See Table 1.

TABLE 1

| Sequence of primers used in this study | | |
|---|---|---|
| Primer | Sequence (5'-3') | SEQ ID NO |
| Fcp1_FlkAF | CGGGATCCCGGATTTCTTGGGTCATTTCTT | SEQ ID NO: 3 |
| Fcp1_FlkAR | GCTCTAGAGCTTCTCTTTCAATGGTATTAG | SEQ ID NO: 4 |
| Fcp1_FlkBF | CCCAAGCTTGGGCGTTCACCTTTTGAGAGCGA | SEQ ID NO: 5 |
| Fcp1_FlkBR | GGACTAGTCCGCTTCAATCGACCGTTTCCA | SEQ ID NO: 6 |
| Spc_Xba5 | GCTCTAGAAACGCGTCCCGAGC | SEQ ID NO: 7 |
| Spc_Hind3 | CCCAAGCTTAACGCGTAAAGTAAGCACC | SEQ ID NO: 8 |
| Fcp1_AscF | GGCGCGCCTGGATCATTGAATAGTCTAT | SEQ ID NO: 9 |
| Fcp1_AscR | GGCGCGCCAAGGATCTTGGTTCGTAAAA | SEQ ID NO: 10 |
| LipL32-45F | AAGCATTACCGCTTGTGGTG | SEQ ID NO: 11 |
| LiL32-286R | GAACTCCCATTTCAGCGATT | SEQ ID NO: 12 |
| LipL32-189p | [6-FAM]AAAGCCAGGACAAGCGCCG[BHQ1a-Q] | SEQ ID NO: 13 |
| GAPDH_R | GGTTCACACCCATCACAAACAT | SEQ ID NO: 14 |
| GAPDH_F | GGTGGAGCCAAGAGGGTCAT | SEQ ID NO: 15 |
| GAPDH_P | [6-FAM]ATCTCCGCACCTTCTGCTGATGCC [BHQ1a-Q] | SEQ ID NO: 16 |

For complementation, the fcp1 gene together with its predicted promoter, was amplified with primers Fcp1_AscF and Fcp1_AscR from *L. interrogans* strain Fiocruz L1-130. The amplified product, after digestion with AscI, was cloned into the suicide pSW29T_TKS2 plasmid (Picardeau, 2008, Appl Environ Microbiol 74, 319-322), which carries a kanamycin-resistant Himar1 transposon. Random insertion mutagenesis by conjugation was carried out in *L. interrogans* strain Fiocruz L1-130 fcp1$^-$ and strain LV 2756 motility deficient, as previously described (Murray et al., 2009, Infect Immun 77, 810-816). Semi-random PCR was used for identification of the transposon insertion site (Murray et al., 2009, Infect Immun 77, 810-816).

For whole-cells lysates, PFs purification and Cryo-ET experiments, *Leptospira* cultures were grown to a late log-phase and prepared as previously described (Lourdault et al., 2011, Infect Immun 79, 3711-3717; Trueba et al., 1992, J Bacteriol 174, 4761-476). Pictures and videos were done under a Zeiss AxioImager. M2 dark field microscopy with AxioCam MRm camera, and analyzed using the AxioVision 4.8.2 software (Carl Zeiss Microscopy LLC).

Flagella Preparation.

Purification of the periplasmic flagella (PFs) was performed by modification of a previous reported protocol (Trueba et al., 1992, J Bacteriol 174, 4761-476). Briefly, 300 mL of a broth culture of late-logarithmic-phase cells (approximately $5\times10^8$ cells/ml) were harvested and centrifuged at 8,000×g for 20 min at 4° C. The cell pellet was resuspend and washed in 28 mL of with PBS. The cell pellet was then resuspend in 30 mL of sucrose solution (0.5 M sucrose, 0.15 M Tris, pH 8.0), and centrifuged at 8,000-×g for 15 minutes. The pellet was resuspend in 8 mL of sucrose solution, and stirred on ice for 10 minutes. To remove the spirochete outer membrane sheath, 0.8 mL of a 10% Triton X-100 solution (1% final concentration) was added and the mixture was stirred for 30 minutes at room temperature, and 80 μL solution of Lysozyme (10 mg/mL) was added slowly and stirred on ice for 5 minutes. Before a 2 h stirring at room temperature, 0.8 mL of EDTA solution (20 mM, pH 8.0) was added slowly. After, 160 μL of $MgSO_4$ solution (0.1M), and 160 μL of EDTA solution (0.1M, pH 8.0) were added, both with intervals of 5 minutes with stirring at room temperature. The suspension was centrifuged at 17,000×g for 15 minutes, and the supernatant fluid was mixed well with 2 mL of PEG 8000 solution (20%) in 1M NaCl), and kept on ice for 30 minutes. After centrifugation at 27,000×g for 30 minutes, the pellet was resuspend in 3 mL of $H_2O$, and a new centrifugation was performed, at 80,000×g for 45 minutes. The final pellet, consisting of purified PFs, was suspended in 1 mL of $H_2O$ and stored at 4 C.

Gel Electrophoresis, Immunobloting and Protein Analysis.

SDS/PAGE and Western blotting were carried out as previously described ((Lourdault et al., 2011, Infect Immun 79, 3711-3717). Antibodies α-FlaA1 were used as positive control in the western blot of the mutants. Cell lysates, and polyclonal antibodies were prepared as described (Croda et al., 2008, Infect Immun 76, 5826-5833). For the western-blot with vaccinated animals, a pool of sera from hamsters 21 days after vaccination with the *L. interrogans* fcp1$^-$ and a pool of sera from hamsters vaccinated with heat-killed bacteria was used as primary antibodies against whole-cell extracts of *L. interrogans* Fiocruz L1-130, Manilae, Canicola and Pomona.

Mass spectrometry analysis (MS+MS/MS) of the whole cell lysates and PFs preparation of the *L. interrogans* strain LV 2756 motile and strain LV 2756 motility deficient were carried out from fragments of the polyacrylamide gel stained with coomassie blue, according to protocols of the Proteomics Platform of the Institute Pasteur, Paris, France. Two independent experiments for each sample and strain were performed.

Electron Microscopy.

Culture in late log-phase (5 mL) was centrifuged at 3.000 rpm for 15 min at 4° C. The supernatant was removed and 5 mL of fixative containing 2% glutaraldehyde and sodium cacodylate buffer (pH 7.4) 0.1M was added to the pelleted cells. The cells were fixed for 1 h at 4° C. and then placed on coverslips treated with poly-L-lysine. After this step, the cells were post-fixed with 1% osmium tetroxide and treated with a graded series of ethanol solutions. The samples were critical point drying, sputter coating with gold and examined using a JEOL 6390LV scanning electron microscopy (SEM).

Preparation of purified PFs (10 μL) was allowed to adsorb for 60 s onto a copper grid coated with Formvar 400 mesh. The grid was washed three times with 0.1M sodium cacodylate and then negatively stained with 2% (w/v) phosphotungstic acid (PTA) pH 7.2. Grids were observed using a JEOL JEM1230 transmission electron microscope (TEM) operating at 80 keV.

For the diameter measurement of the flagella, twenty random pictures were taken from each group on the same magnification (200.000×), using a Gatan camera and software DigitalMicrograph® for acquisition. Four different measurements of the PFs thickness were taken from each strain, using the ImageJm1.45s software. The averages of those measurements were used for comparison between groups.

Immuno-EM Assays.

Purified PFs (15 μL) were allowed to adsorb for 10 min in glow-discharged copper grids coated with Formvar 300 mesh. Immediately the grids were blocked for 2 min in 0.1% BSA, and incubated for 20 min with 1:10 dilution (0.1% BSA) of primary antibody. Polyclonal antibodies anti-FlaA1, FlaA2, anti-FlaB1, and Fcp1 were used as primary antibodies. The grids were washed 3 times with ultrapure water, and blocked again in 0.1% BSA for 2 min. Secondary antibody 5 nm gold-conjugated Protein A (PAG) was used in a dilution of 1:50 (0.1% BSA), incubated for 20 min. The grids were washed three times with ultrapure water and then negatively stained with 2% PTA pH 7. Grids were observed using a Philips TECNAI 12 BioTwin II operating at 80 keV. Images were acquired on Soft Imaging System Morada camera using iTEM image acquisition software.

Cryo-Electron Tomography and 3-D Reconstruction.

Viable bacterial cultures were centrifuged to increase the concentration to ~$2\times10^9$ cells/nil. Five-microliter samples were deposited onto freshly glow-discharged holey carbon grids for 1 min. The grids were blotted with filter paper and rapidly frozen in liquid ethane using a gravity-driven plunger apparatus as previously described (Raddi et al., 2012 J Bacteriol 194, 1299-1306). The resulting frozen-hydrated specimens were imaged at −170° C. using a Polara G2 electron microscope (FEI Company, Hillsboro, Oreg.) equipped with a field emission gun and a 4K×4K charge-coupled-device (CCD) (16-megapixel) camera (TVIPS; GMBH, Germany). The microscope was operated at 300 kV with a magnification of ×31,000, resulting in an effective pixel size of 5.6 Å after 2×2 binning. Using the FEI batch tomography program, low-dose single-axis tilt series were collected from each bacterium at −6 μm defocus with a cumulative dose of ~100 $e^-/Å^2$ distributed over 87 images, covering an angular range from −64° to +64°, with an angular increment of 1.5°. Tilted images were aligned and then reconstructed using IMOD software package. In total, 10, 15 and 17 reconstructions were generated from WT, fcp1 mutant and complemented strains, respectively.

A total of 1392 segments (192×192×96 voxels) of flagellar filaments were manually identified and extracted from 42 reconstructions. The initial orientation was determined using two adjacent points along the filament. Further rotational alignment was performed to maximize the cross-correlation coefficient. Averaging was carried out with a merging procedure in reciprocal space (Raddi et al., 2012 J Bacteriol 194, 1299-1306).

Tomographic reconstructions were visualized using IMOD. Reconstruction of cells were segmented using 3D modeling software Amira (Visage Imaging). Three-dimensional segmentations of the cytoplasmic, outer membranes and flagellar filaments were manually constructed.

Translocation Assays with MDCK Cells.

A translocation assay was performed according to a protocol modified from that described by Figueira et al. (Figueira et al., 2011, BMC Microbiol 11, 129). MDCK cells at a concentration of $2\times10^5$ cells in 500 μl of DMEM were seeded onto 12-mm-diameter transwell filter units with 3-μm pores (COSTAR). Monolayers were incubated at 37° C. in 5% CO2 for 3 to 4 days with daily changes in media until the transepithelial resistance (TER) reached a range of 200 and 300 Ω/cm2, as measured with an epithelial voltohmmeter (EVOM, World Precision Instruments, Sarasota, Fla.). The TER for polycarbonate filters without cells was approximately 100 Ω/cm2. The upper chamber of the transwell apparatus was inoculated with a multiplicity of infection (MOI) of 100 leptospires by adding 500 μL of bacteria, which were resuspend in 1:2 v/v ratio of DMEM and EMJH media. Duplicate transwell chamber assays were performed for each leptospiral strain tested. Aliquots were removed from lower chamber (100 μl) at 2, 4, 6 and 24 hours and the number of leptospires were counted in triplicate by using the Petroff-Hausser counting chamber (Fisher Scientific). The ability of leptospires to translocate MDCK polarized monolayers was determined by calculating the proportion of leptospires in the lower chamber in comparison to the initial inoculums for duplicate assays at each time point.

Virulence Studies.

All hamster experiments used 3-6 week-old Golden Syrian male hamsters from Harlan Laboratories, and were conducted following the National Institutes of Health guidelines for housing and care of laboratory animals. All the procedures were performed under animal protocols approved by the Yale University Institutional Animal Care and Use Committee and Gonçalo Moniz Research Center, Fiocruz. The bacterial challenges in animals were performed using doses from 10-$10^8$ leptospires by IP route and dose of $10^8$ leptospires by CJ route.

For the experiments of virulence, one group of 8-10 animals for each of the six strains was inoculated intraperitoneally (IP) with a high-dose inoculum ($10^8$ leptospires) in 1 ml of EMJH medium. For the LD50 experiments, two groups of 4 animals were inoculated IP with doses of 100 and 10 leptospires, for the strains LV2756 motile, LV2756 motility-deficient fcp1$^+$, Fiocruz L1-130 WT and Fiocruz L1-130 fcp1$^{-/+}$. For the strains LV2756 motility-deficient and Fiocruz L1-130 fcp1$^-$, animals were infected with doses of $10^8$ and $10^7$ leptospires.

Animals were monitored twice daily for clinical signs of leptospirosis and death, up to 21 days post-infection. Moribund animals were immediately sacrificed by inhalation of $CO_2$.

Dissemination Studies.

For the experiments of dissemination, one group of six animals for strains LV2756 motile and LV2756 motility deficient was inoculated intraperitoneally with $10^8$ leptospires in 1 ml of EMJH medium. After 1 hour and 4 days post-infection, sub-groups of two animals were euthanized.

With the same strains, a conjunctival infection was performed by centrifugation of 30 ml culture of leptospires for 10 minutes at 1000 rcf and using an inoculum of $10^8$ leptospires in 10 μl of EMJH medium instilled in the left eye conjunctiva using a micropipette. Groups of four animals were infected and two were euthanized after 7 days of infection for each strain tested. In those experiments, a group of two animals was left as a positive control.

To understand the dissemination of the fcp1⁻ mutant using a subcutaneous (SC) route, we infected groups of 10 animals with $10^7$ bacteria of *L. interrogans* Fiocruz L1-130 wild-type, fcp1⁻ mutant and heat-killed wild-type by subcutaneous route. For each group of infection two animals were euthanized after 1, 4, 7, 14 and 21 days post-infection.

Animals were monitored twice daily for clinical signs of leptospirosis and death, up to 21 days post-infection. Moribund animals were immediately sacrificed by inhalation of $CO_2$.

The necropsy for the dissemination study was made as follows. Animals were sacrificed by inhalation of $CO_2$ and placed on their backs slightly inclined in the dissecting tray. After sterilization of the abdomen with alcohol 70% and using sets of sterile instruments, the internal organs were exposed, including the heart and lungs. All blood was collected directly from the heart in a Vacutainer® K2 EDTA Tubes (BD Diagnostics, Franklin Lakes, N.J.) and glass serum tubes, using a 5 ml syringe with a 21 G needle. A 21 G butterfly needle affixed to a 60 ml syringe containing sterile saline 0.85% was then inserted into the left ventricle. The right atrium was snipped to allow the residual blood and normal saline to leave the body during the perfusion. Each hamster was perfused with 100 ml of saline solution. After perfusion, right pulmonary lobe, right dorsocaudal hepatic lobe, spleen, right kidney and right eye were carefully removed. All the tissues were collected into cryotubes and immediately placed into liquid nitrogen before being stored at −80° C. until extraction. Blood, kidney, liver, lung, spleen and eye were analyzed.

Using scissors and scalpels, 25 mg of lung, liver, kidney cortex, and eye, 10 mg of the spleen, and 200 μl of blood were aseptically collected. DNA was extracted using the Maxwell® 16 Tissue DNA purification kit (Promega Corporation, Madison, Wis.), after homogenization with Bullet Blender (Next Advance, Averill Park, N.Y.).

Quantitative Real Time PCR.

Bacterial quantification was determined using an ABI 7500 (Applied Biosystems, Foster City, Calif.) and Platinum Quantitative PCR SuperMix-UDG (Invitrogen Corporation, Carlsbad, Calif.). The lipL32 gene was amplified using a of primers and probe (Table 1), according to protocol previously described (Stoddard et al., 2009, Diagn Microbiol Infect Dis 64, 247-255). Hamster housekeeping gene glyceraldehyde-3-phophate dehydrogenase (GAPDH) was used as a control for PCR inhibitors and to monitor nucleic acid extraction efficiency. The forward primer of GAPDH_F and GAPDH_R were selected to amplify a fragment that was detected by the probe, GAPDH_P. A sample with a threshold cycle (Ct) value between 16 and 21 was considered as positive and further analyzed by real-time PCR targeting lipL32. In case of a negative sample, a new DNA extraction was performed. For each organ, the DNA was extracted from one sample and the Real Time PCR was performed in duplicate. Considering the amount of tissue that was used for DNA extraction, an equation was applied to express the results as the number of leptospires per gram of tissue or per ml of blood/water.

Immunization Studies.

Groups of 7-10 hamsters were immunized with $10^7$ bacteria with *L. interrogans* Fiocruz L1-130 wild-type, motility-deficient fcp1⁻ mutant and heat-killed bacteria by SC route and challenged 21 days later with a lethal dose of a range of serovars whose virulence has been well-characterized in our laboratory (Table 2). Animals were infected by conjunctival inoculation, which mimics the natural route of infection, with a dose of $10^8$ bacteria. Animals were monitored twice daily for clinical signs of leptospirosis and death, up to 21 days post-infection. Moribund animals were immediately sacrificed by inhalation of $CO_2$.

TABLE 2

Strains used in vaccine experiments

| Species | Serovar | Strain | $LD_{50}$* |
|---|---|---|---|
| *L. interrogans* | *Copenhageni* | Fiocruz L1-130 | <10 |
| *L. interrogans* | *Canicola* | Kito | <10 |
| *L. interrogans* | *Pomona* | PO-06-047 | <10 |
| *L. interrogans* | *Manilae* | L495 | <10 |
| *L. kirschneri* | *Grippotyphosa* | RM52 | <10 |

*$LD_{50}$ for intraperitoneal inoculation of hamsters

Passive transfer experiments. Golden Syrian Hamsters were immunized with one dose of the *L. interrogans* Fioruz L1-130 fcp1⁻ live-attenuated vaccine, and bled the animals after 21 days to obtain hyper-immune sera. Then 3 mL of the hamster sera was transferred intraperitoneally (IP) to a group of 3 naïve hamsters 16 hours prior to lethal challenge of $10^7$ leptospires by IP route in with the heterologous strain *L. interrogans* Manilae. A control group of 3 hamsters were passive-transferred with 3 mL of sera from non-vaccinated animals. Animals were monitored twice daily for clinical signs of leptospirosis and death, up to 14 days post-infection. Moribund animals were immediately sacrificed by inhalation of $CO_2$.

Statistical Analysis.

Data were graphed and analyzed using GraphPad Prism 5.0c (GraphPad Software, La Jolla, Calif.). Fisher's exact test and analysis of variance (ANOVA) were performed to assess statistical significance of differences between pairs of groups and multiple groups, respectively. P values <0.05 were considered to be significant.

The Results of the experiments disclosed herein are now described.

Identification of a *L. interrogans* Motility-Deficient Mutant.

The cloning process of *L. interrogans* serovar Copenhageni strain 2756 in solid EMJH yielded two distinct sizes of colony growth (FIG. 1A). Large colonies, identified after 3 weeks of incubation of the plates at 30° C., had the same morphological shape and motility characteristics as the parental strain when observed by dark field microscopy (FIG. 1B), whereas the small colonies, identified after 4 weeks of incubation had a linear appearance, lacking the characteristic hook-shaped end of leptospires, had no translational motility, and grew as long chains with incomplete division planes (FIG. 1B). Analysis under scanning electron microscopy showed that the motility-deficient cells retained their spiral body morphology (FIG. 1C).

Negative stain electron microscopy of purified PFs from both clones showed that the motility-deficient clone had straight flagella, different from the characteristic extensive coiled flagella of the motile clone (FIG. 1D).

A Novel Protein Involved in Leptospiral Motility.

Figure 2B:
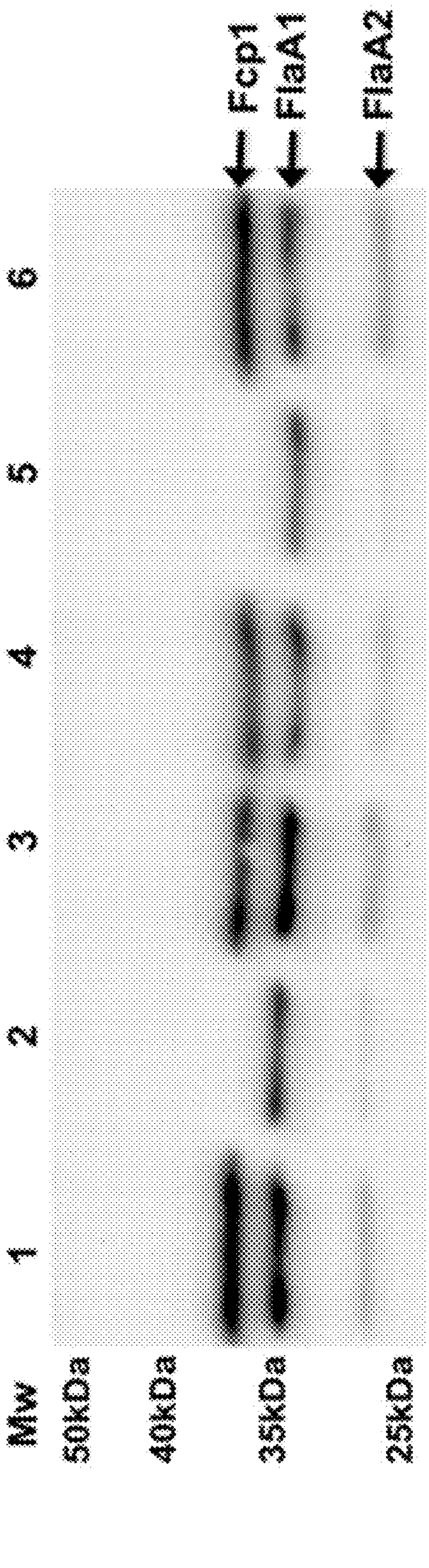
FIG. 2B is a western blot of purified PFs. Western Blot was probe with polyclonal antibodies against Fcp1, and polyclonal antibodies against FlaA1. Arrows indicate the position of the proteins identified by specific polyclonal antibodies.

SDS-PAGE of whole cell lysates and PFs preparations from the motile clone of *L. interrogans* strain LV 2756 showed a band of 36 kDa that lacks in the strain LV 2756 motility-deficient clone (FIG. 2B). Mass spectrometry (MS) analyses of this 36 kDa protein band from the motile clone showed the presence of 7 and 4 different peptides in whole cell lysates and purified PFs, respectively. One of these peptides corresponded to a hypothetical protein coded by the gene LIC13166 from *L. interrogans* serovar Copenhageni strain Fiocruz L1-130. Similar analyses using SDS-PAGE gel fragments around the 36 kDa region with proteins obtained from whole cell lysates and purified PFs from the motility-deficient clone revealed no peptide corresponding to LIC13166.

This gene is present in all *Leptospira* species sequenced so far, including the saprophyte one, *L. biflexa* serovar Patoc, which has an orthologous gene with 76% nucleotide identity. The protein encoded by LIC13166 has been described as the $13^{th}$ most abundant among all cell proteins in *L. interrogans* (Malmstrom et al., 2009, Nature 460, 762-765). However, no orthologous genes outside the Leptospiraceae family are known. It has a predicted signal peptide (first 25 amino acids), and it was previously described as an outer membrane, OmpL36 (Pinne and Haake, 2009, PLoS One 4, e6071) and a putative coagulase involved in the pathogenesis. More recently, it was showed that it has no ligand-binding activity against the main host-tissue components, but it is recognized by acute and convalescent leptospirosis patients' sera as well as by sera from hamsters infected with leptospires. Two-dimensional gel electrophoresis analyses showed that it was overexpressed under in vivo-like conditions (iron limitation with presence of fetal bovine serum), and also showed higher levels of expression in pathogenic serovars. Given the correlation of its expression with the normal structure of leptospiral PFs, the protein encoded by LIC13166 was renamed as Flagellar coiling protein (Fcp1), predicted to have 306 amino acids.

Figure 3:
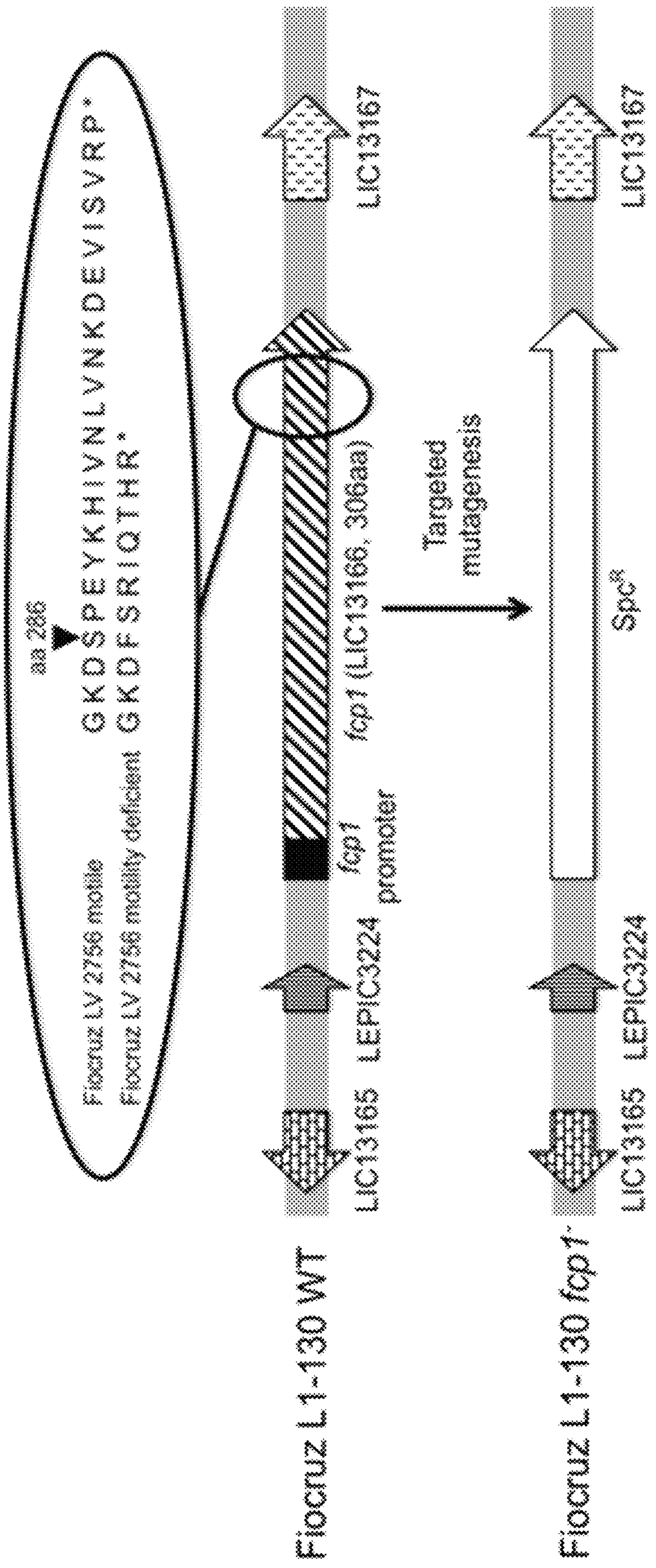
FIG. 3 diagrams the inactivation of the fcp1 gene. Schematic representation of the genotype of *L. interrogans* Fiocruz L1 130 WT and *L. interrogans* Fiocruz L1 130 fcp1$^-$, showing the allelic exchange of the fcp1 gene by Spc$^r$ cassette. The highlighted area is indicating the region of the fcp1 gene where the mutation occurred in the Fiocruz LV 2756 motility-deficient, showing also the result regarding the protein expression.

Purified PFs from the motile clone showed the expression of Fcp1 as revealed by western blot analyses using a monospecific anti-Fcp1 polyclonal antibody (FIG. 2B). In contrast, no Fcp1 expression was detected in the motility-deficient clone, neither in whole-cell lysates nor purified PFs (FIG. 2B), indicating that the spontaneous mutation abolished expression of Fcp1 protein in this clone. DNA sequencing of the fcp1 gene in both mutants showed an insertion of a deoxythymidine in the position 3876851 (corresponding to amino acid 286) of the *L. interrogans* serovar Copenhageni strain Fiocruz L1-130 genome, introducing a reading frame shift in the motility-deficient clone gene that lead to a premature stop codon at amino acid position 294 (FIG. 3).

Allelic Exchange Mutagenesis and Complementation.

To confirm that the phenotype observed in the motility-deficient clone was caused by the mutation in the fcp1 gene, a gene replacement construct was generated by homologous recombination (FIG. 3), which could be confirmed by PCR. Allelic exchange resulted in the null mutant Fiocruz L1-130 $fcp1^-$, which has a motility-deficient phenotype when compared to parental strain, Fiocruz L1-130 WT.

Complemented strains were obtained by random mutagenesis using Himar1 transposon carrying the fcp1 gene from *L. interrogans* strain Fiocruz L1-130. By semi-random PCR, the transposon insertion sites in 4 transformants were identified for the motility-deficient strain LV 2756, eventually selecting the clone LV 2756 motility-deficient $fcp1^+$. This mutant had the transposon inserted in a non-coding region between the genes LIC12898 and LIC12899, which encodes for a hypothetical and a cytoplasmic membrane protein, respectively.

For the strain Fiocruz L1-130 $fcp1^-$, 3 transformants were obtained, and the clone Fiocruz L1-130 $fcp1^{-/+}$ was selected, with the transposon inserted in a non-identified region. However, sequencing results by semi-random PCR allowed designing primers that confirmed the insertion of the transposon, identifying several stop codons for the 6 frames in the region, and indicated that the transposon was inserted in a non-coding region.

SDS/PAGE and Western blot analyses showed that the fcp1 mutant lacks the expression of Fcp1, and that the complementation was able to rescue its normal expression (FIG. 2). Analysis of the mutant Fiocruz L1-130 $fcp1^-$ by motility assay, dark field and electron microscopy confirmed that its phenotype was identical to the LV 2756 motility-deficient clone. Furthermore, expressing Fcp1 in the mutants restored the hook-shaped end of the cells, and their normal translational motility as seen by the analyses of both complemented strains (FIG. 1A-C). Purified PFs obtained from Fiocruz L1-130 $fcp1^-$ had the same straight phenotype as that of the LV 2756 motility-deficient clone, and the coiled morphology was restored by the complementation of the fcp1 gene, resulting in identical features as observed in the LV 2756 motile and Fiocruz L1-130 WT clones (FIG. 1D). Fcp1 was detected in purified PFs preparation in Fiocruz L1-130 WT and complemented mutant strain, confirming its localization in flagella. Altogether these findings indicate that the lack of Fcp1 was responsible for the disappearance of the flagellum coil structure associated with a loss of cell motility.

Fcp1 is Necessary for the Formation of the PFs Sheath in *Leptospira* Interrogans.

The diameter of the purified PFs was analyzed from all six different strains obtained, to determine if Fcp1 was involved in the structure of leptospiral flagella. Four different in-vitro measurements were made from each of the twenty images of the PF of each strain. The average diameter of PFs purified from the LV 2756 motile and Fiocruz L1-130 WT clones were 21.5±1.99 nm, and 22.8±2.01 nm, respectively, whereas that of the PFs purified from the LV 2756 motility-deficient and L1-130 $fcp1^-$ clones were 16.27±2.88 nm, and 17.63±0.92 nm, respectively. The differences between the wild-type and the mutants' diameters were statistically significant ($p<0.0001$). Expressing Fcp1 in $fcp1^-$ mutants allowed the restoration of the wild-type average diameter of the PFs, showing no significant difference with respect to the wild-type.

Figures 4A, 4B, 4C, 4D, 4E, 4F, 4G, 4H:
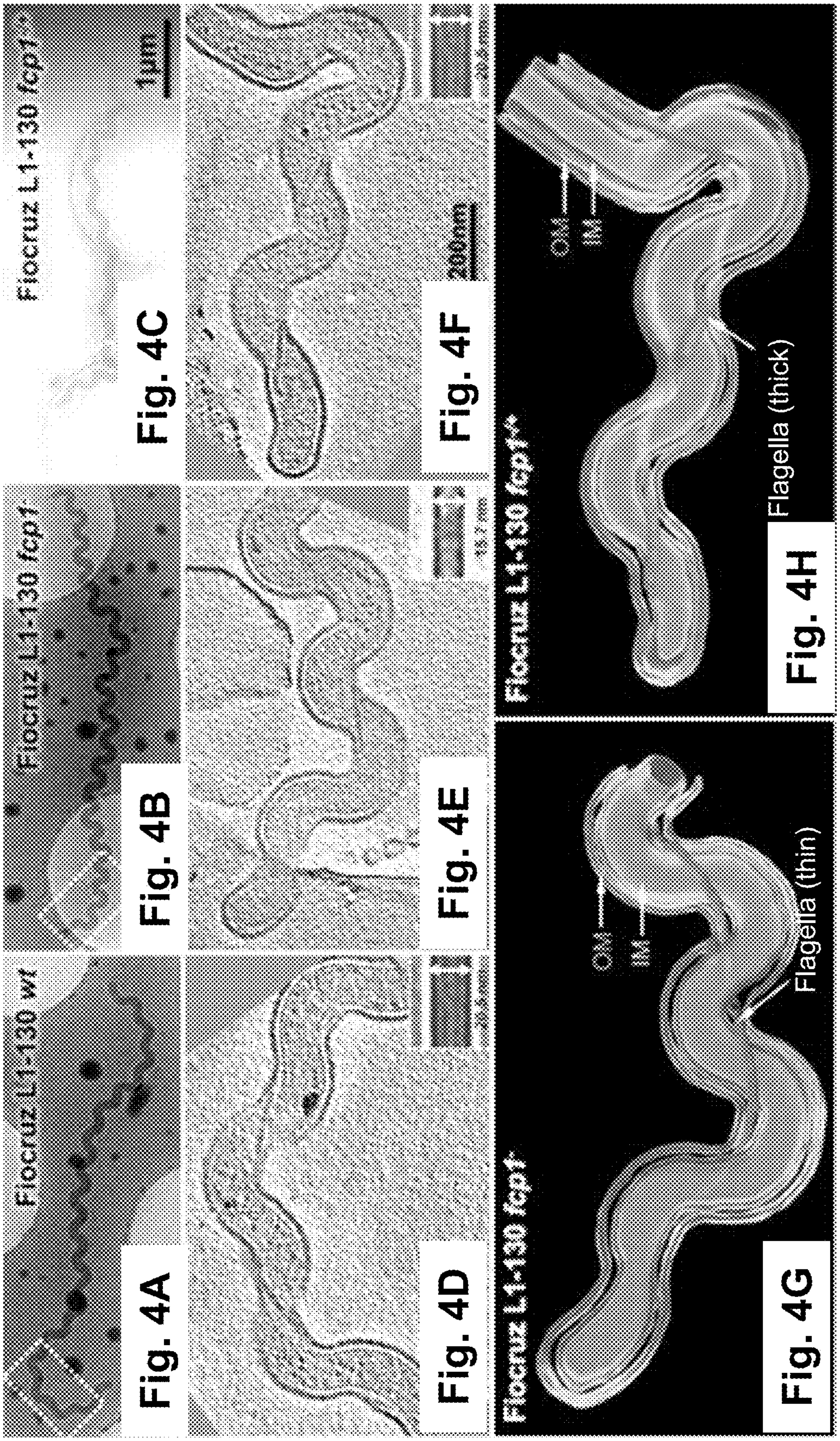
FIG. 4A shows the cell morphology with a cryo-ET analysis of the Fiocruz L1-130 WT.
FIG. 4B shows the cell morphology with a cryo-electron tomography (ET) analysis of the Fiocruz L1-130 fcp1$^-$.
FIG. 4C shows the cell morphology with a cryo-ET analysis of the Fiocruz L1-130 fcp1$^{-/+}$.
FIG. 4D is a tomographic reconstruction showing one slice of Fiocruz L1-130 WT. Flagellar filaments are indicated by arrays, and the pictures are from the averaged maps of PFs segments from each of the strains. The diameter of the flagellar filament in Fiocruz L1-130 fcp1$^-$ mutant is 15.7 nm, in contrast to the diameter of 20.5 nm in wild-type organisms or complemented cells.
FIG. 4E is a tomographic reconstruction showing one slice of L1-130 fcp1$^-$ and L1-130 fcp1$^{-/+}$. Flagellar filaments are indicated by arrays, and the pictures are from the averaged maps of PFs segments from each of the strains. The diameter of the flagellar filament in Fiocruz L1-130 fcp1$^-$ mutant is 15.7 nm, in contrast to the diameter of 20.5 nm in wild-type organisms or complemented cells.
FIG. 4F is a tomographic reconstruction showing one slice of L1-130 fcp1$^{-/+}$. Flagellar filaments are indicated by arrays, and the pictures are from the averaged maps of PFs segments from each of the strains. The diameter of the flagellar filament in Fiocruz L1-130 fcp1$^-$ mutant is 15.7 nm, in contrast to the diameter of 20.5 nm in wild-type organisms or complemented cells.
FIG. 4G shows the surface renderings of 3-D reconstructions of Fiocruz L1-130 fcp1$^-$ with prominent structural features including the outer membrane (OM), cytoplasmic membrane (IM) and flagellar filament.
FIG. 4H shows the surface renderings of 3-D reconstructions of Fiocruz L1-130 fcp1$^{-/+}$, with prominent structural features including the outer membrane (OM), cytoplasmic membrane (IM) and flagellar filament.

In order to examine the cellular morphology and the flagellar structure of the wild-type, $fcp1^-$ mutant and complemented strain, three-dimensional reconstructions in situ of intact organisms were generated using cryo-electron tomography (cryo-ET). The results confirmed that the flagellar filament of the $fcp1^-$ mutant was significantly thinner than that those in the wild-type and complemented strain (FIG. 4).

Figures 5A, 5B:
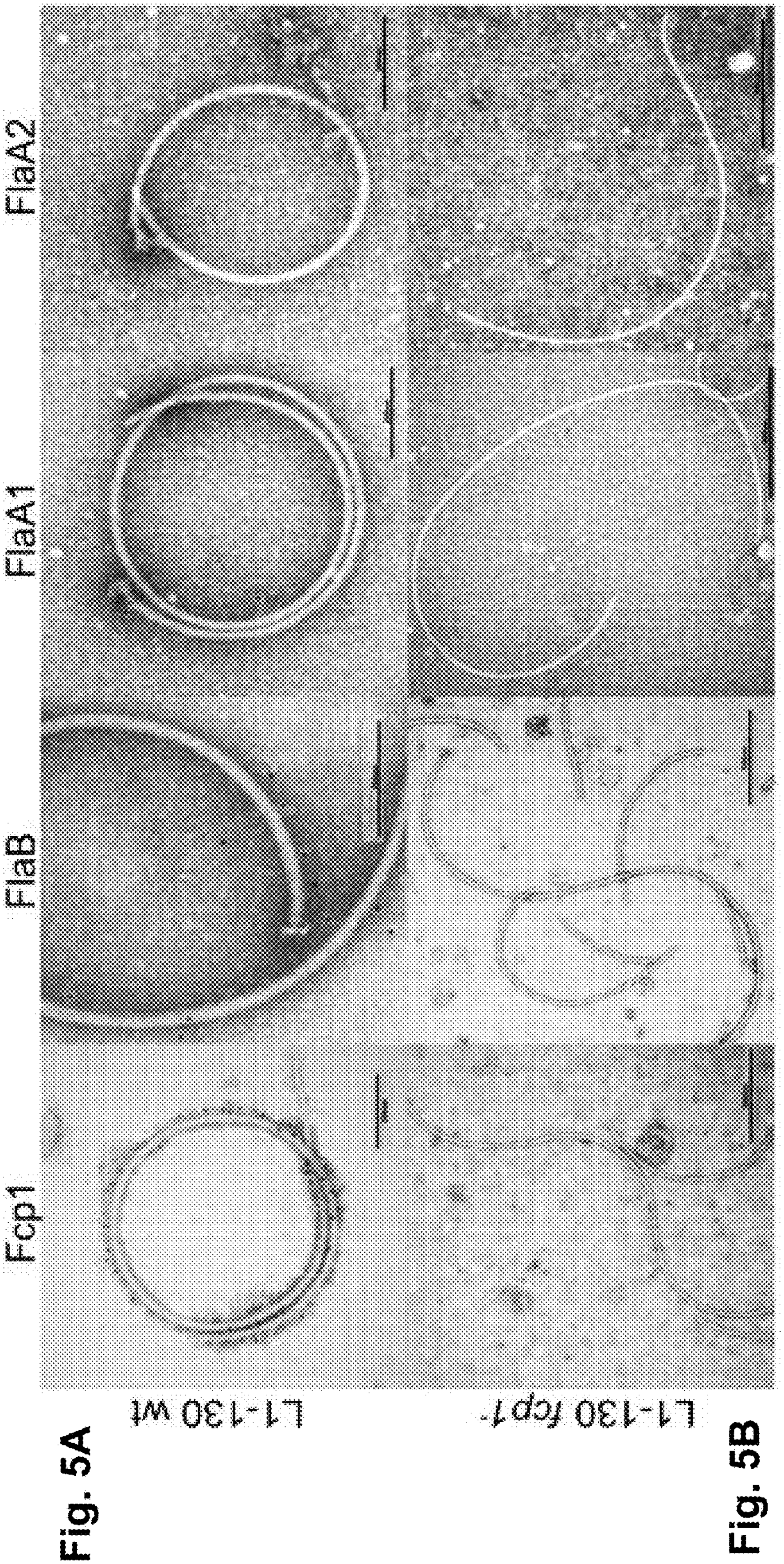
FIG. 5A is a panel of scans showing an immuno-EM assay using purified PFsI preparation from Fiocruz L1-130 WT. The PF was labeled with antibodies against Fcp1 (α-Fcp1), FlaB1 (α-FlaB1), FlaA1 (α-FlaA1), and FlaA2 (α-FlaA2). Secondary antibody anti-rabbit conjugated with 5 nm gold nanoparticles was used to detect bound antibodies. PF were visualized using 2% PTA negative staining.
FIG. 5B is a panel of scans showing an immuno-EM assay using purified PFsI preparation from Fiocruz L1-130 fcp1$^-$. The PF was labeled with antibodies against Fcp1 (α-Fcp1), FlaB1 (α-FlaB1), FlaA1 (α-FlaA1), and FlaA2 (α-FlaA2). Secondary antibody anti-rabbit conjugated with 5 nm gold nanoparticles was used to detect bound antibodies. PF were visualized using 2% PTA negative staining.

Immuno-EM assays using antibodies anti-Fcp1 indicated that this protein is being expressed on the surface of the PFs, evenly distributed along its whole length in the Fiocruz WT strain (FIG. 5). The fcp1-mutant didn't show any expression of the Fcp1 protein. Antibodies anti-FlaB1, anti-FlaA1 and anti-FlaA2 were used as control, however there was no binding in either of the two strains used (FIG. 5). This assay indicates that the lack of antibody binding Fcp1 protein is because no Fcp1 proteins were surfaced exposed.

Attenuated, Motility Deficient Strains are Unable to Translocate Across Tissue Barriers.

Figure 7:
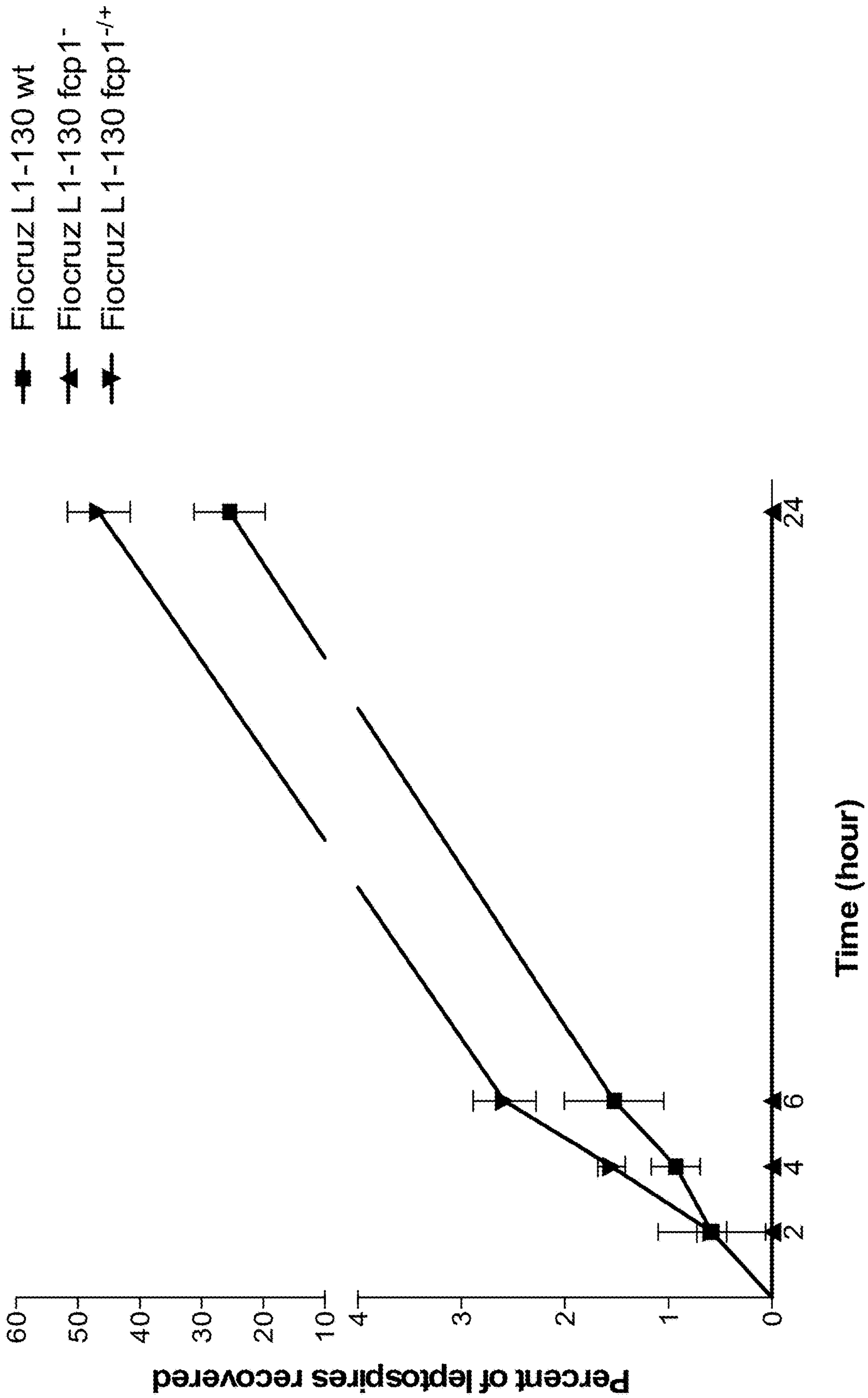
FIG. 7 is a graph showing the results of translocation assays and the percent recovery of leptospires after inoculation of polarized MDCK cell monolayers with Fiocruz L1-130 WT, Fiocruz L1-130 $fcp1^-$, and Fiocruz L1-130 $fcp1^{-/+}$. Bacteria were inoculated in the upper chamber of MDCK cell monolayer transwell chambers. Translocating bacteria was quantified by counting bacteria in the lower chamber. Assays were performed at 2, 4, 6, and 24 hours after addition of bacteria. The assays were performed in triplicate, and results are expressed as mean±SD.

The lack of expression of Fcp1 leads to a reduced ability to translocate a monolayer of MDCK cells, as showed by the results obtained with the translocation assay (FIG. 7). The strain Fiocruz L1-130 $fcp1^-$ was unable to translocate across the monolayer of MDCK cells after 24 h of incubation, while after 2 h of incubation 0.6% of both Fiocruz L1-130 WT and Fiocruz L1-130 $fcp1^{-/+}$ were recovered, reaching a recovery rate of 25.5% and 46.7%, respectively, after 24 h of incubation.

Motility is Essential for Leptospiral Virulence.

To determine if Fcp1 plays a role in the pathogenesis of the disease, groups of 8-10 hamsters were infected intraperitoneally (IP) with $10^8$ leptospires (in three independent experiments), with all the 6 strains described in this study (Table 3). The strains LV 2756 motile and Fiocruz L1-130 WT clones were able to kill all animals between the $6^{th}$ and $8^{th}$ day post-infection (Table 3).

In three experiments, animals challenged with strain LV 2756 motility-deficient clone survived after 21 days post-infection. All animals infected with strain Fiocruz L1-130 $fcp1^-$ survived in two of the experiments (Table 3), but 50% died in one of the experiments, between days 6 and 10 post-infection. The complementation of the fcp1 gene was able to restore the phenotype of virulence, and animals challenged with strains LV 2756 motility-deficient $fcp1^+$ and Fiocruz L1-130 $fcp1^{-/+}$ were able to kill 100% of the animals between days 6 and 10 post-infection (Table 3).

TABLE 3

Virulence of strains of *L. interrogans* serovar *Copenhageni* after hamster where inoculated intraperitoneally with $10^8$ leptospires§

| Bacterial Strain | Mortality (%) | Time to death (days) |
|---|---|---|
| Fiocruz LV2756 motile | 100 | 6, 6, 6, 6, 6, 6, 6, 8 |
| Fiocruz LV2756 motility-deficient | 0* | — |
| Fiocruz LV2756 motility-deficient $fcp1^+$ | 100 | 6, 6, 8, 8, 9, 9, 10, 10 |
| Fiocruz L1-130 WT | 100 | 6, 6, 6, 8, 8, 8, 8, 8 |
| Fiocruz L1-130 $fcp1^-$ | 0¶* | — |
| Fiocruz L1-130 $fcp1^{-/+}$ | 100 | 6, 6, 6, 8, 8, 8, 8, 8 |

§Results are showed for one of three independent experiments. Group of 08 animals were challenged using an intraperitoneal infection dose of $10^8$ leptospires. All the experiments showed equivalent results.
¶Mortality rate of 50% in one experiment for this specific strain (p = 0.038)
*Statistically significance difference when compared with wild-type results (p = 0.00007)

To assess the difference showed between strains Fiocruz L1-130 $fcp1^-$ and the LV 2756 motility-deficient strains, and also to determine if the complemented strains were still highly virulent as the wild-type ones, two independent experiments of $LD_{50}$ were performed, with two groups of four hamsters inoculated by the IP route. Animals challenged with the strains LV 2756 motile, LV 2756 motility-deficient $fcp1^+$, Fiocruz L1-130 WT and Fiocruz L1-130 $fcp1^-$ were infected with doses of 100 and 10 leptospires, and animals challenged with the LV 2756 motility-deficient and Fiocruz L1-130 $fcp1^-$ strains were infected with doses of $10^8$ and $10^7$ leptospires. As previously described (Croda et al., 2008, Infect Immun 76, 5826-5833), the $LD_{50}$ for the strain Fiocruz L1-130 WT was lower than 10 leptospires, and the same result was found for the strain LV 2756 motile and the two complemented strains, while the LV 2756 motility-deficient and Fiocruz L1-130 $fcp1^-$ strains had a $LD_{50}$ of $>10^8$ leptospires and $10^8$ leptospires respectively (Table 4), showing that motility is paramount for virulence, and Fcp1 plays a key role.

TABLE 4

$LD^{50}$ of *L. interrogans* serovar *Copenhageni* after hamsters were inoculated intraperitoneally with $10^8$ leptospires§

| Bacterial Strain | $LD^{50}$ |
|---|---|
| Fiocruz LV2756 motile | 4.64 leptospires |
| Fiocruz LV2756 motility-deficient | $>10^8$ leptospires¶ |
| Fiocruz LV2756 motility-deficient $fcp1^+$ | 4.64 leptospires |
| Fiocruz L1-130 WT | <10 leptospires* |
| Fiocruz L1-130 $fcp1^-$ | $10^8$ leptospires |
| Fiocruz L1-130 $fcp1^{-/+}$ | 10 leptospires |

§Results are showed for one of three independent experiments. Three groups of 4 animals for each strain were challenged using an intraperitoneal infection dose of $10^8$ leptospires. All the experiments showed equivalent results.
¶All the animals infected with $10^8$ leptospires survived
*All the animals infected with 10 leptospires died Motility-Deficient Strains, Although Attenuated, Induces a Transient Bacteremia after Experimental Infection.

To determine the dissemination of leptospires in the hamster model, quantitative real time PCR was performed in tissues of animals infected with $10^8$ leptospires using the IP and conjunctival (CJ) inoculation route. Groups of IP infected hamsters were euthanized 1 hour, and 4 days after infection.

Figures 6A, 6B, 6C:
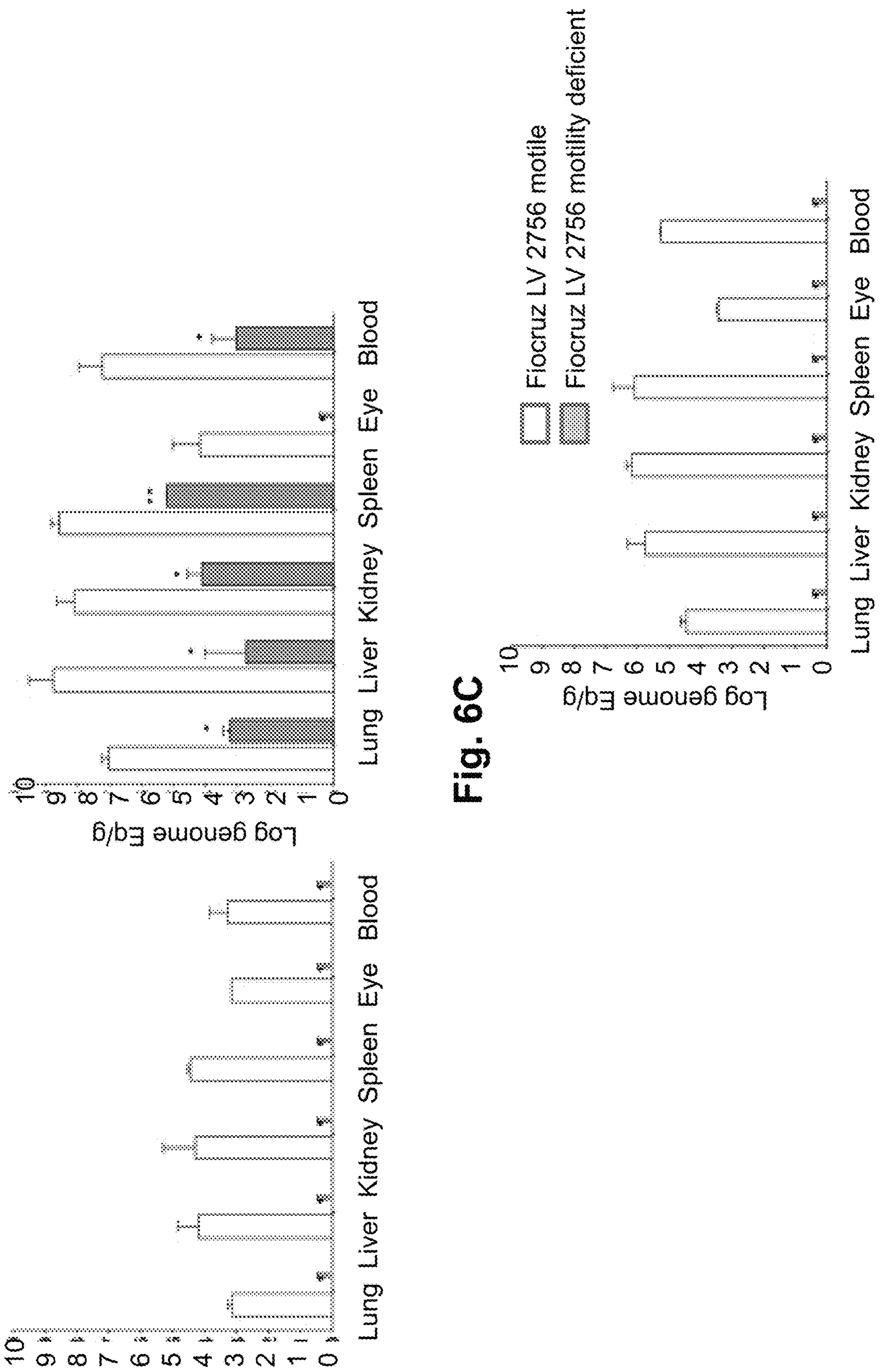
FIG. 6A is a graph showing the dissemination of leptospires in tissues from hamsters infected with the Fiocruz LV 2756 motile (white columns), and the Fiocruz LV 2756 motility-deficient (gray columns) determined by quantitative real time PCR. The analysis of the tissues was performed one day post-infection.
FIG. 6B is a graph showing the dissemination of leptospires four days post-infection with $10^8$ leptospires infected by intraperitoneal route.
FIG. 6C is a graph showing the dissemination of leptospires after 7 days post-infection with $10^8$ leptospires infected by conjunctival route. Bacterial load for each tissue was calculated based on the mean result of two perfused hamsters. Each column in FIGS. 5A-5C represents the mean (logarithmic scale) of two independent experiments. Error bars in FIGS. 5A-5C represent the standard deviation.

All control animals infected with the strain LV 2756 motile clone died after 5-6 days of infection, while the animals infected with the strain LV 2756 motility-deficient survived after 30 days post-infection. All tissues of strain LV 2756 motile analyzed were positive after 1 hour for the presence of the agent, with a range of $2\times10^3$-$5\times10^4$ leptospires/g of tissue, while the strain LV 2756 motility-deficient were undetectable (FIG. 6A). After 4 days of infection, the burden of the strain LV 2756 motile ranged from $1.5\times10^4$ to $6\times10^8$ leptospires/g in the eye and liver, respectively. Although after 4 days post-infection, leptospires were detectable in all the tissues when inoculated with strain LV 2756 motility-deficient, the burden of leptospires was significantly lower in comparison with the motile clone, ranging from $1.7\times10^5$ to $5\times10^2$ in the spleen and liver, respectively (FIG. 6B). Analysis after 30 days of tissues from animals that survived of the LV 2756 motility-deficient challenge showed no detectable leptospires in any tissue, and there was no detection of leptospires in the eye of infected animals at any time point (FIG. 6A-B).

When hamsters were infected with $10^8$ leptospires by CJ route, none of the analyzed tissues infected with the strain LV 2756 motility-deficient were positive for the presence of leptospires after seven days post-infection (FIG. 6C), while for the LV 2756 motile all the tissues were positive, with a burden ranging from $4\times10^3$ leptospires/g in the eye to $2\times10^6$ leptospires/g in the kidney (FIG. 6C), with the control animals dying after 8-9 days post-infection. All the control animals infected with the LV 2756 motility-deficient survived, and there was no detection of leptospiral DNA after 30 days in any of the tissues.

Figure 8:
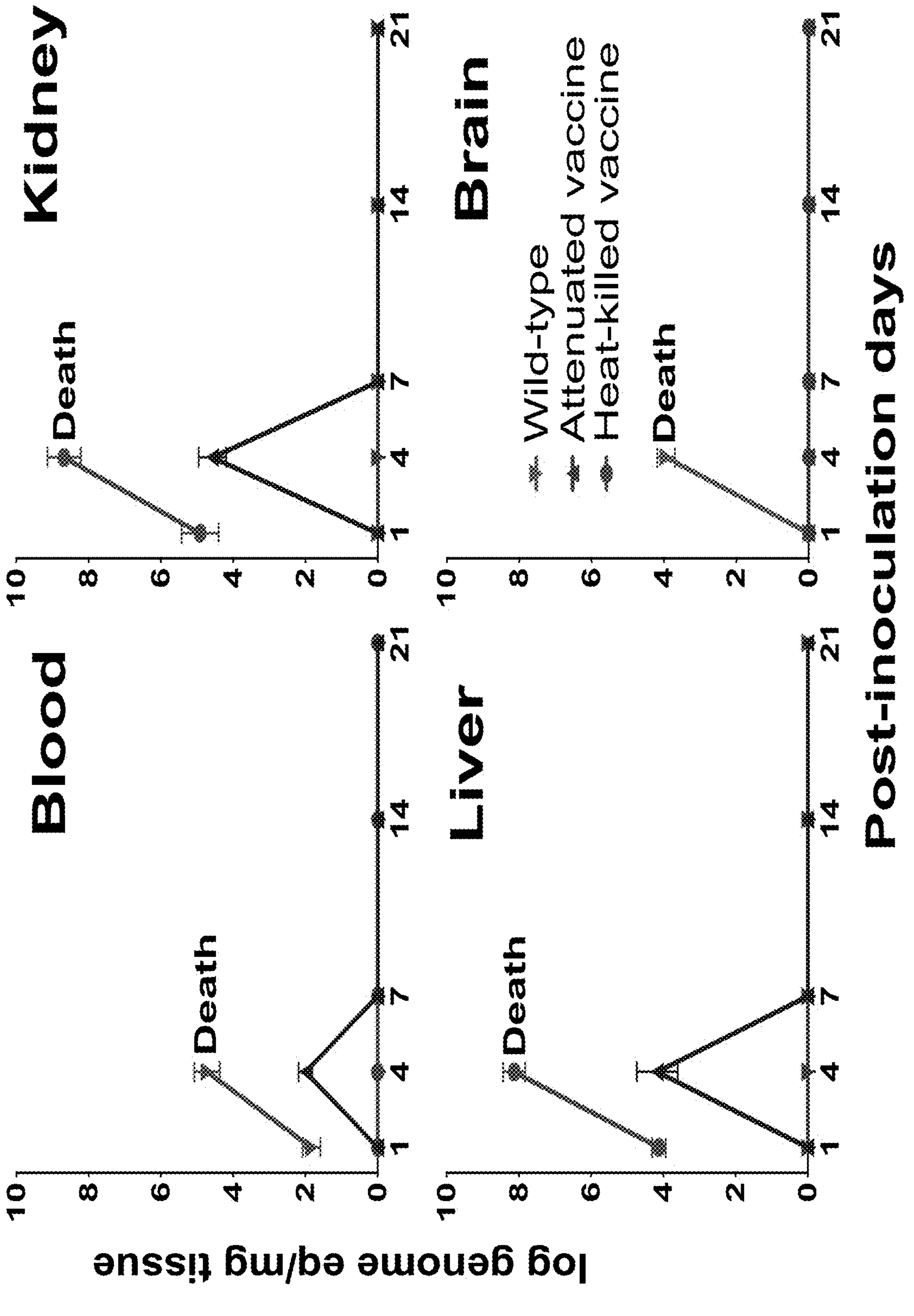
FIG. 8 is a graph showing the kinetics of dissemination after subcutaneous inoculation with $10^7$ bacteria of L1-130 wild-type, attenuated vaccine and heat-killed vaccine in blood, kidney, liver and brain between days 1 up to 21-days post infection.

Although the motility-deficient mutant has a strong phenotype of attenuation, it was still able to cause a transient systemic infection after IP (FIG. 6B) and conjunctival (FIG. 8) infection, which was cleared 7 days after inoculation (FIG. 8). There was no evidence of DNA dissemination in any tissues after SC vaccination with heat-killed bacteria (FIG. 8).

Immunization with Attenuated, Motility-Deficient fcp1-Strains Confers Protection Against Leptospirosis Due to Homologous and Heterologous Serovars.

It was also determined if motility-deficient fcp1-mutant may serve as a candidate for a live attenuated vaccine since:

1) deletion of the fcp1-gene renders mutants unable to produce disease or renal colonization, 2) the transient bacteremia produced by needle inoculation may be sufficient to induce robust and long-lasting immune responses, and 3) attenuated leptospires may elicit cross-protective immune responses against protein moieties conserved across pathogenic *Leptospira*. This was evaluated by administering hamsters with a single subcutaneous dose of heat-killed, wild-type bacteria and live fcp1-mutant of *L. interrogans* serovar Copenhageni, and then infecting hamsters three weeks after immunization with a lethal dose of four serovars of *L. interrogans* species, serovars Copenhageni, Manilae, Canicola and Pomona, and the serovar Grippotyphosa, which belongs to *L. kirschneri*, a different pathogenic species of the *Leptospira* genus.

As expected, immunization with heat-killed bacteria conferred homologous protection against challenge infection with *L. interrogans* serovar Copenhageni, but did not induce heterologous protection against infection with a serovar *L. interrogans* serovar Manilae (Tables 5 and 6). Protection experiments using a different challenge strain, *L. kirschneri* sorovar Grippotyphosa, indicate that the cross-protection conferred by the live-attenuated vaccine also protects against a different species of *Leptospira*, other than *L. interrogans*.

TABLE 5

Protection conferred by immunization with attenuated fcp1− mutant in hamster model of leptospirosis

| Immunization Scheme | Challenge Serovar | No. Animals | % Protection (No. Died) | P-value |
|---|---|---|---|---|
| fcp1− | Copenhageni* | 9 | 100 (0) | <0.001 |
| Heat-killed | | 9 | 67 (0) | <0.01 |
| PBS | | 8 | — (8) | — |
| fcp1− | Manilae** | 9 | 100 (0) | <0.001 |
| Heat-killed | | 9 | 11 (7) | NS |
| PBS | | 8 | — (8) | — |
| fcp1− | Pomona** | 8 | 100 (0) | <0.001 |
| PBS | | 8 | — (8) | — |
| fcp1− | Canicola** | 8 | 100 (0) | <0.001 |
| | | 8 | — (8) | — |
| fcp1− | Grippotyphosa** | 7 | 100 (0) | 0.02 |
| PBS | | 7 | 29 (5) | — |

Representative results of one of four* and one of two** experiments

In contrast, immunization with live fcp1-mutants conferred complete protection against infection with the five serovars (Tables 5 and 6). Although it doesn't seem to have protection against colonization (Table 6), it's important to mention that hamsters are extremely susceptible to leptospirosis where less than 10 leptospires are able to kill the animals. For that reason, this experimental model may underestimate the efficacy with respect to this endpoint. Nonetheless, these findings indicate that a single dose of a live attenuated vaccine elicited cross-protective immunity against serovars belonging to *L. interrogans*, the species, which encompasses the majority of serovars of human and animal health importance, but also can confer protection to serovars of different species among the *Leptospira* genus (Table 6).

TABLE 6

Immunization with attenuated fcp1$^-$ mutant strain protects hamsters against lethal challenge with $10^8$ bacteria via conjunctival route.

| | Challenge | No. | | Vaccine Efficacy (%, 95% CI) | |
|---|---|---|---|---|---|
| Vaccine | Serovar | Expt | Animals | Death | Death/Colonization |
| fcp1$^-$ | *Copenhageni* | 4 | 6, 7, 9, 9 | 100 (90.4-100) | 51.6 (34.8-68) |
| | *Manilae* | 3 | 7, 9, 9 | 100 (88.4-100) | 20 (8.4-39.6) |
| | *Pomona* | 2 | 8, 8 | 100 (82-100) | 0 (0-17.1) |
| | *Canicola* | 2 | 7, 8 | 100 (82.9-100) | 26.7 (10.5-52.4) |
| | *Grippotyphosa* | 2 | 7, 7 | 100 (80.3-100) | 34 (19.6-58.7) |
| Heat- | *Copenhageni* | 2 | 8, 9 | 58.9 (36-78.4) | 35.3 (17.2-56.4) |
| killed | *Manilae* | 2 | 8, 9 | 5.6 (0-27.7) | 0 (0-15.5) |

Immunization with Additional Attenuated, Motility-Deficient Strains Confers Protection Against Leptospirosis Due to Homologous and Heterologous Serovars.

In order to verify that other motility-deficient mutants could be potential candidates for an attenuated live vaccine, a Himar1 random mutant of *L. interrogans* serovar Manilae with disruption of gene flaA2 was tested. This mutant lacks the expression of FlaA2 and FlaA1 proteins described also to be part of the sheath of the leptospiral flagella apparatus. Previous studies showed that this mutant is also avirulent in the hamster model of infection. Using the same protocol as for the fcp1$^-$ mutant, a group of 16 animals with the FlaA mutant were vaccinated, and afterward they were challenged for 21 days with the homologous Manilae strain and the heterologus L1-130 Fiocruz strain.

TABLE 7

Protection conferred by immunization with attenuated flaA1$^-$/flaA2$^-$ mutant in hamster model of leptospirosis

| Immunization Scheme | Challenge Serovar | No. Animals | % Protection (No. Died) | P-value |
|---|---|---|---|---|
| flaA1−/flaA2− | *Manilae* | 8 | 100 (0) | <0.001 |
| PBS | | 8 | — (8) | — |
| flaA1−/flaA2− | *Copenhageni* | 8 | 100 (0) | <0.001 |
| PBS | | 8 | — (8) | — |

The flaA mutant of *L. interrogans* serovar Manilae (also having a disruption of the flagellar genes, thus lacking of expression of FlaA1 and FlaA2) was another potential candidate for live-attenuated vaccine. After vaccination with this strain animals were challenged with a homologous (*L. interrogans* serovar Manilae) and heterologous strain (*L. interrogans* serovar Copenhageni), and similar results were observed as with the live-attenuated fcp1$^-$ vaccine, with complete protection against death after homologous and heterologous challenge (Table 7). All the animals vaccinated survived the challenge, indicating that the FlaA mutant was able to confer cross-protection against infection.

Figure 9B:
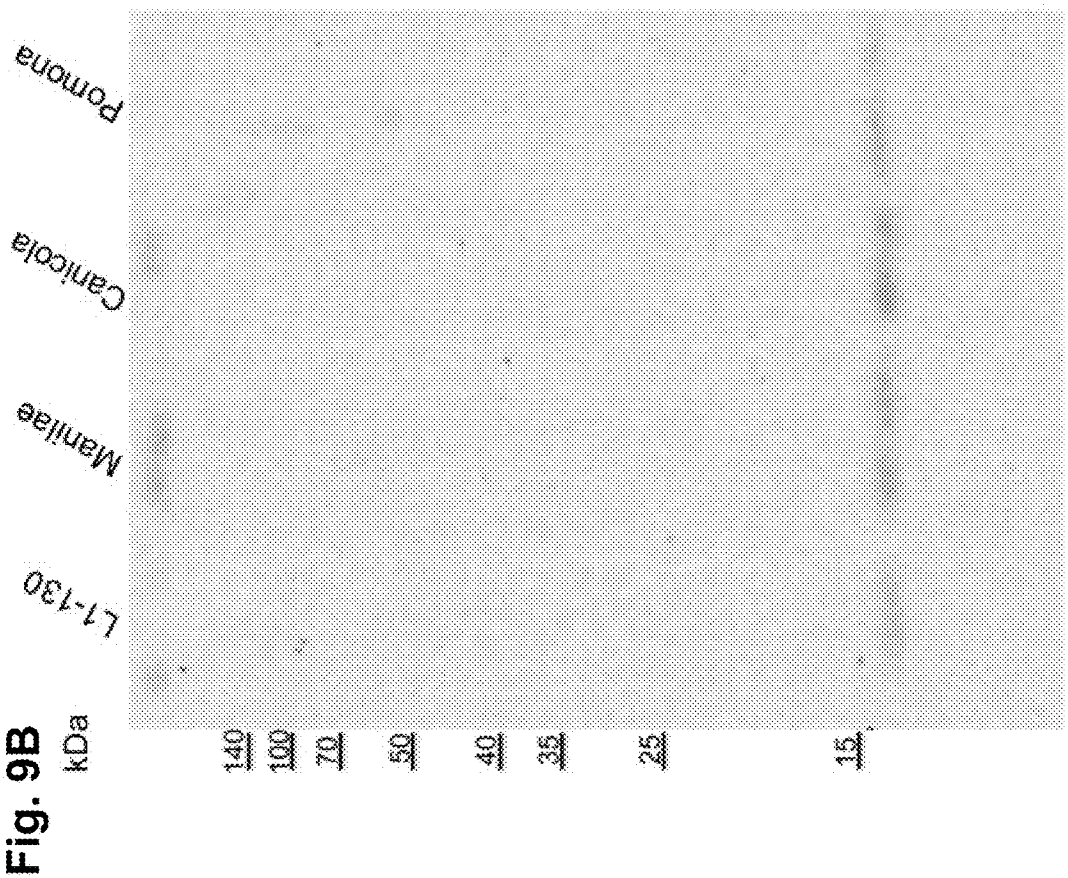
FIG. 9B is an image of a western blot illustrating the profile of a pool of sera from hasmters 21 days post-vaccination with the heat-killed *L. interrogans* L1-130 vaccine (before challenge).
Figure 9A:
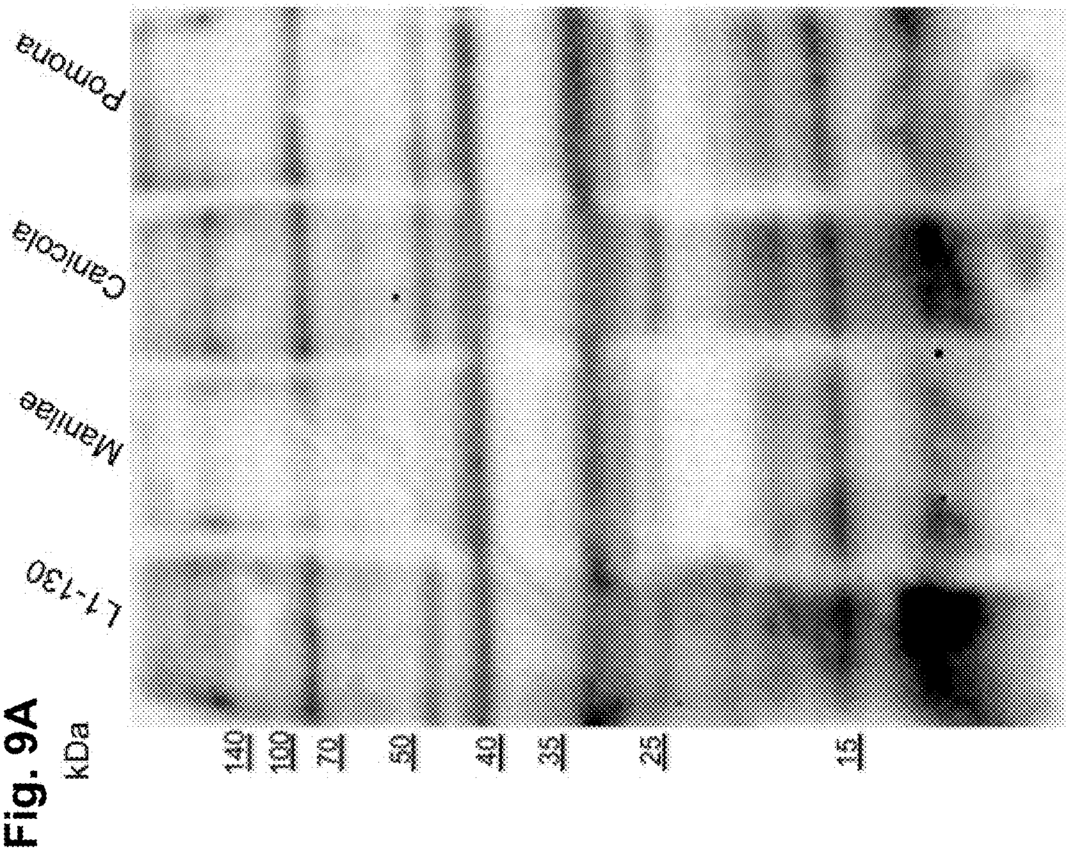
FIG. 9A is an image of a western blot illustrating the profile of a pool of sera from hamsters 21 days post-vaccination with the live-attenuated $fcp1^-$ vaccine (before challenge).

Immunization with the Attenuated, Motility-Deficient Strains Induce a Robust Antibody Response:

The attenuated vaccine induced a weak agglutinating antibodies (GMT, 256; SD, 152.9-429.3) to the homologous serovar, Copenhageni, and undetectable MAT titers against heterologous serovars. In contrats, western-blot experiments with the sera from hamsters after vaccination with the live-attenuated fcp1$^-$ vaccine showed a strong reaction agains several leptospiral proteins for all the different serovars (FIG. 9A), whereas sera from animals vaccinated with the heat-killed bacteria doesn't seem to produce antibodies against leptospiral proteins (FIG. 9B). These results indicate that anti-*Leptospira* protein antibodies, and not agglutinating antibodies, are the correlate of vaccine-mediated, cross-protective immunity.

Passive Transfer of Antibodies Generated Against Attenuated, Non-Motile Strains Confers Protection Against Leptospirosis.

Figure 10:
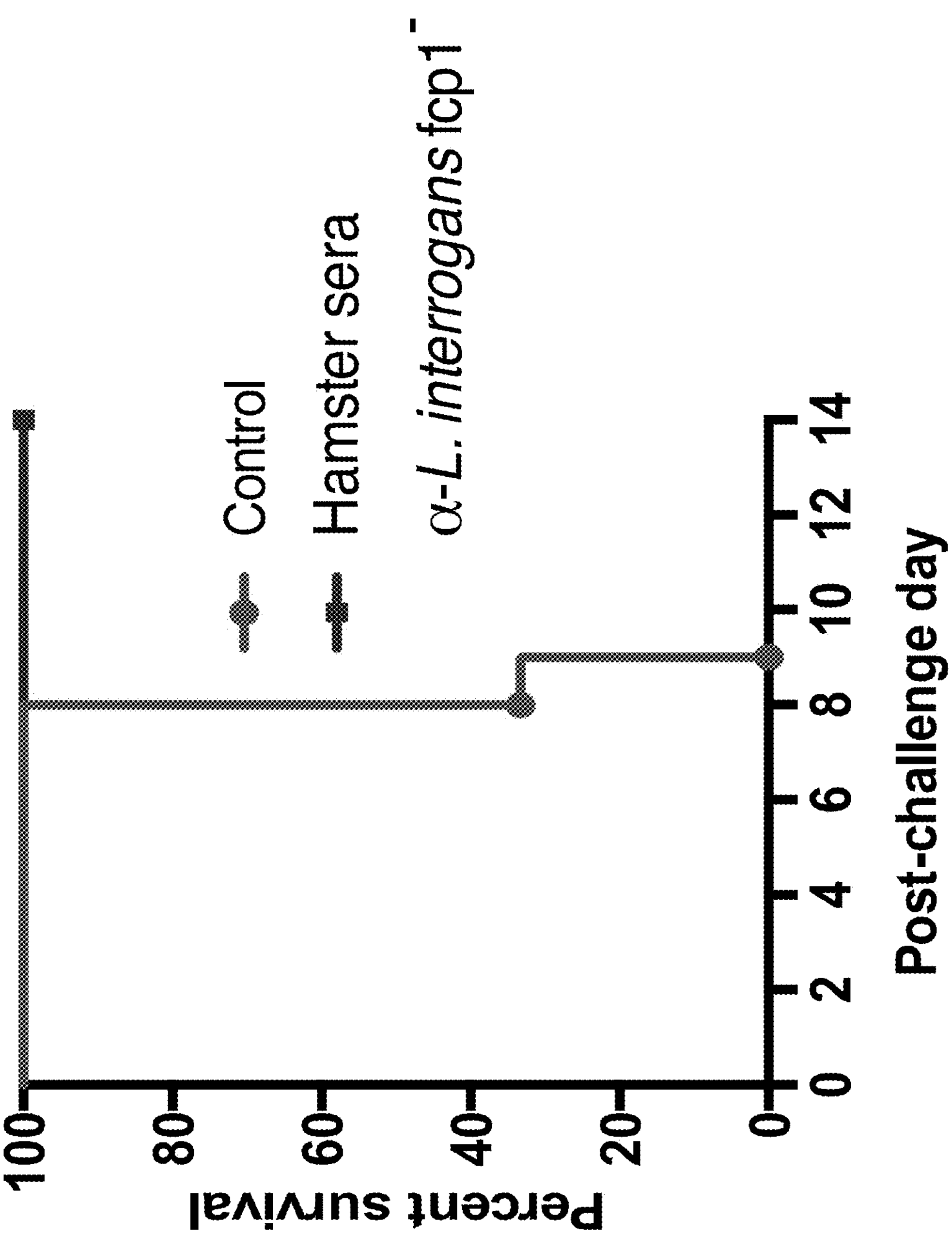
FIG. 10 is a survival curve of passive transfer with sera from hamster vaccinated with *L. interrogans* serovar Fiocruz L1-130 $fcp1^-$ after intraperitoneal heterologous challenge with $10^7$ bacteria of *L. interrogans* strain Manilae.

To better understand the role of antibodies for the cross-protection, sera from vaccinated hamsters was passive-transferred to naïve animals before lethal challenge. All the control animals, which were passive-transferred with non-vaccinate sera, died in between days 8 and 9 post-infection, whereas all the passively transferred hamsters with the anti-attenuated vaccine sera survived up to 14 days post-infection (FIG. 10). This result demonstrates that the transfer of antibodies confers protection against heterologous infection, indicating that antibodies against *Leptospira* protein have a major role on the cross-protection conferred by this vaccine.

In the 1960s, motility-deficient clones describing basic morphological differences of hooked and straight cells correlated to small colonies in solid media and virulence attenuation in the hamster model, were reported for *Leptospira* spp. However, at that time it was impossible to determine the genetic lesion causing the aberrant phenotype, and since non-pathogenic strains could also present hook-shaped ends, the authors concluded that the results were a coincident simultaneous variation in virulence and visible shape. Bromley et al. (Bromley and Charon, 1979, J Bacteriol 137, 1406-1412) characterized a motility-deficient mutant with straight cell ends and forming uncoiled PFs obtained by chemical mutation. The authors did suggest that PFs were involved in the shape of the cell ends, but they could not rule out the possibility that mutations were affecting regulatory genes.

The mutant strain described herein appeared via spontaneous mutation, leading to a motility-deficient phenotype, and the identification of the specific mutation. Mass-spectrometry analyses led to the identification of a single gene disruption in the motility-deficient clone. Both LV 2756 motile and LV 2756 motility-deficient clones had their whole genomes sequenced (data not shown), confirming the mutation into a gene encoding the Fcp1 protein. The results confirm the relationship between the structure of the PFs, the cell shape, and motility.

Fcp1 is involved in formation of the hook-shaped ends of *Leptospira* cells, and therefore key for translational motility. Photographic analysis of wildtype cells during movement showed that the protoplasmic cell cylinder was flexible and bended in response to the gyrations of the hooks. Previous results showed that the hook-shaped end of *Leptospira* provides counter-torque, but its gyration is not essential for propulsion, and that leptospires could have translational motility only with the spiral end shape. This observation was supported with mathematical modeling, showing that the minimum energy configuration in the absence of applied forces or torques is a hook shape, caused by a clockwise rotation of the PFs. It is also known that in translating leptospires, the gyration of the cells' end caused a spiral-shaped wave sufficient to propel the cells forward, caused by a counterclockwise gyration of the PFs. However, the gyration of the spiral-shaped ends in the fcp1$^-$ mutants, was either too slow or not large enough to yield sufficient thrust for the bacteria to translate, similar to what happens with *T. phagedenis* in low-viscosity media.

Fcp1 is associated with the PFs filament structure in *Leptospira* species, and essential for the formation of its sheath. Genetic analysis of spirochetal flagellin proteins showed that stiffer PFs can deform the cell cylinder, and larger deformations produced more thrust. The fcp1$^-$ mutants generated a flagellar structure that when purified lost its natural super-coiled form, leading to the inability to change the cell ends. Thus, the cells were not able to translate.

A recent MS-based study showed that Fcp1 is the 13$^{th}$ most abundant protein in the whole proteome of Fiocruz L1-130 WT, and although this protein was never described as being involved in the structure of flagella, its abundance is consistent with a structural function. Trueba et al. (Trueba et al., 1992, J Bacteriol 174, 4761-4768) showed that the PFs sheath of *Leptospira* contains at least one protein with molecular mass of 36 kDa tightly associated with the core.

According to the results, it was found that the FlaA proteins and the core protein FlaB1 are associated with the purified PFs even in the fcp1$^-$ mutants, as shown by MS and western-blot analyses. In vitro and in situ analyses (FIG. 4) showed that the flagella diameter of the fcp1$^-$ mutants was significantly smaller than that of the wild-type and complemented strains.

Furthermore, immuno-EM assays indicated that this protein was associated with the surface of the PFs in the Fiocruz L1-130 WT strain (FIG. 6). The same phenotypes were observed in a mutant of fcp1 gene in the saprophyte *L. biflexa* serovar Patoc (data not shown). Taken together, these observations corroborate the hypothesis that Fcp1 was essential for the formation of the PFs sheath in *Leptospira* spp., and that the lack of this protein, led to the impaired motility of the cells.

The function of spirochetes' flagellar sheath is still unclear, and the presence and composition of the sheath differs among species. It is known that FlaA impacts the shape and the stiffness of PFs and its helicity in *B. hyodysenteriae*, but it is present only in the basal body region in *B. burgdorferi*. A recent study showed that FlaA proteins are not involved in the formation of the flagellar sheath in *Leptospira*. Furthermore, the immuno-EM assays did not show expression of FlaA and FlaB1 proteins on the surface of PFs filament with or without Fcp1 expression (FIG. 6). However, the mutants that lacked expression of both FlaA proteins, did express Fcp1 (data not shown), but lacked hook-shaped ends and translational motility that rendered straight PFs when purified.

*Leptospira* has four different FlaB proteins, and previous disruption of FlaB1 gene on *L. biflexa* serovar Patoc yielded cells with no flagella. Nevertheless, as in other spirochetes, it is not clear the distribution and interaction of these proteins are within the core and sheath of PFs. This indicates that the formation of coiled flagella and hook-shaped ends, and their involvement in translational motility, is complex having more than one protein involved. The interaction among these proteins seems to be important for these phenotypes, although it is yet to be understood how this interaction works.

It has been shown that rotation of the PF leads to changes in the cell shape caused by resistive forces between PFs and cell body, and those changes drive the movement of spirochetes. For that reason, if there were any perturbation in the flagellar structure itself and/or the interaction of the flagella with the cell body, it would generate a cell with impaired motility.

The present data shows that the lack of Fcp1 led to the assembly of thinner PFs, probably due to the total or partial lack of the sheath. This may cause the loss of its natural tensile strength and the inability to generate enough thrust for translational motility of the cell.

However, mathematical modeling, based on *B. burgdorferi* motility, recently evaluated the interaction of the PFs with the peptidoglycan layer (PG) of the bacterial cell body. It was thought that a fluid layer must separate both structures and that motion occurs by resistance that is generated from fluid drag, instead of friction. Considering that the flagella sheath is responsible for the interaction of the PFs with the PG, it is conceivable that its loss could lead to an impaired adherence of those two structures, thus causing the inability to slip and engage properly, eventually resulting in abolishment of proper gyration of the cell end. It is still unclear if the phenotype observed in the present mutants is due to the event of one of these hypotheses, but a reciprocal action of both is more likely.

Motility is essential for virulence in *Leptospira*, and it is directly involved in the dissemination of the agent in different tissues. Their unique motility behavior may help these organisms to escape from the innate immune response and rapidly disseminate in mammalian hosts.

A mutant in *L. interrogans* with disruption of the gene encoding a flagellar motor switch protein (FliY) was previously described showing both motility and virulence attenuation, but complementation analyses were not performed. The pathogenesis studies showed that the Fcp1 mutants had an attenuated virulence phenotype, where doses as high as $10^8$ leptospires with those mutants were unable to kill animals, compared to a $LD_{50}$ of 10 leptospires for the wild-type and complemented strains.

Furthermore, it was shown that after infection with the $fcp1^-$ mutants all the animals survived after 30 days of infection with no renal colonization, even if leptospiral DNA could be detected probably because of haematogenous dissemination of non-motile bacteria.

The penetration of the spirochete into the host mucosa is an essential process to establish infection, and motility is, in turn, essential for penetration. Spirochetes have the ability to cross-epithelial barriers, traverse the intercellular matrix, enter into tissues, disseminate, and finally cause systemic infections.

By using a conjunctival (CJ) route for infection, which resembles one natural mode of infection of the agent, the ability of the spirochete to cross the epithelial barrier is critical to reach the bloodstream and disseminate. Despite of the intraperitoneal (IP) infection, no dissemination of the motility-deficient clone was observed using CJ route, and no deaths occurred, whereas all animals infected with the motile-clone showed dissemination and 100% of death. Nevertheless, the $LD_{50}$ for CJ route is 5 logs higher than the IP route indicating that other factors could be acting to prevent the infection like lacrimal fluid, or constant grooming of the animals. However, in vitro studies showed that $fcp1^-$ mutants were not able to translocate mammalian cell monolayers after 24 hours, whereas the wild-type and complemented strain had a translocation rate of 25% and 46%, respectively (FIG. 7). These results indicated that motility was essential for virulence and dissemination and played an important role in the penetration process of the spirochete in the host.

Given their unique morphology and structure, spirochetal motility is unusual and by far one of the most complex motility systems among bacteria. Recent studies showed that the model of the flagellar structure previously described, indicating that FlaA proteins are responsible for the PFs' sheath, does not apply for *Leptospira*. In the studies, one structural protein of the PFs was identified in leptospires involved in the formation of the hook-shaped end, and in the normal coiling of flagella.

Also, the data described herein indicates that Fcp1 is essential for the formation of the flagellar sheath, leading to impaired translational motility, and furthermore, the inability to penetrate tissues to cause infection in animal models.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of stimulating an immune response in a subject in need thereof comprising administering a composition comprising an effective amount of a motility deficient *Leptospira* bacteria to the subject, wherein the *Leptospira* bacteria is deficient in wild-type flagellar-coiling protein 1 (Fcp1).

2. The method of claim 1, wherein the *Leptospira* bacteria are live bacteria.

3. The method of claim 1, wherein the *Leptospira* bacteria are heat-inactivated.

4. The method of claim 1, wherein the *Leptospira* bacteria have attenuated bacterial virulence.

5. The method of claim 1, wherein the composition further comprises an adjuvant.

6. The method of claim 5, wherein the adjuvant is selected from the group consisting of an oil-in-water emulsion, a saponin, a cholesterol, a phospholipid, a CpG, a polysaccharide, variants thereof, and a combination thereof.

7. The method of claim 1, wherein administering the composition comprises producing antibodies against the motility deficient *Leptospira* bacteria.

8. A method for reducing or treating an infectious disease caused by one or more *Leptospira* bacteria in a subject in need thereof comprising administering a composition comprising an effective amount of a motility deficient *Leptospira* bacteria to the subject, wherein the *Leptospira* bacteria is deficient in wild-type flagellar-coiling protein 1 (Fcp1).

9. The method of claim 8, wherein the *Leptospira* bacteria are live bacteria.

10. The method of claim 8, wherein the *Leptospira* bacteria are heat-inactivated.

11. The method of claim 8, wherein the *Leptospira* bacteria have attenuated bacterial virulence.

12. The method of claim 11, wherein the composition further comprises an adjuvant.

13. The method of claim 12, wherein the adjuvant is selected from the group consisting of an oil-in-water emulsion, a saponin, a cholesterol, a phospholipid, a CpG, a polysaccharide, variants thereof, and a combination thereof.

* * * * *